United States Patent
Packer et al.

(10) Patent No.: US 10,204,389 B2
(45) Date of Patent: Feb. 12, 2019

(54) RESCUE PERFORMANCE METRICS FOR CPR AND TRAUMATIC BRAIN INJURY

(71) Applicant: ZOLL Medical Corporation, Chelmsford, MA (US)

(72) Inventors: Richard A. Packer, Westborough, MA (US); Gary A. Freeman, Newton Center, MA (US); Annemarie Silver, Bedford, MA (US)

(73) Assignee: ZOLL MEDICAL CORPORATION, Chelmsford, MA (US)

(*) Notice: Subject to any disclaimer, the term of this patent is extended or adjusted under 35 U.S.C. 154(b) by 671 days.

(21) Appl. No.: 14/296,861

(22) Filed: Jun. 5, 2014

(65) Prior Publication Data
US 2014/0365175 A1    Dec. 11, 2014

Related U.S. Application Data

(60) Provisional application No. 61/833,296, filed on Jun. 10, 2013.

(51) Int. Cl.
| | |
|---|---|
| G01D 21/00 | (2006.01) |
| G06Q 50/22 | (2018.01) |
| G06Q 50/24 | (2012.01) |
| A61B 5/00 | (2006.01) |
| A61B 5/0402 | (2006.01) |
| A61B 5/093 | (2006.01) |
| G06F 19/00 | (2018.01) |
| A61B 5/087 | (2006.01) |
| G09B 23/28 | (2006.01) |

(52) U.S. Cl.
CPC .......... *G06Q 50/24* (2013.01); *A61B 5/0006* (2013.01); *A61B 5/0402* (2013.01); *A61B 5/093* (2013.01); *A61B 5/743* (2013.01); *G06F 19/00* (2013.01); *A61B 5/087* (2013.01); *A61B 2505/01* (2013.01); *G09B 23/288* (2013.01)

(58) Field of Classification Search
CPC ......... A61B 5/0205; A61B 5/11; A61B 5/742; A61B 5/7275; A61B 5/1118; A61H 31/005; A61H 2201/5007; A61H 2201/5043; A61N 1/3925; A61N 1/36135; A61N 1/36585
USPC .... 600/300, 301, 544, 483, 484, 529; 607/4, 607/6, 66, 7, 17, 18
See application file for complete search history.

(56) References Cited

U.S. PATENT DOCUMENTS

| | | | |
|---|---|---|---|
| 6,406,427 B1 | 6/2002 | Williams et al. | |
| 7,299,088 B1* | 11/2007 | Thakor | A61B 5/048 600/544 |
| 2006/0173501 A1* | 8/2006 | Stickney | A61B 5/046 607/5 |
| 2007/0060785 A1* | 3/2007 | Freeman | A61H 31/00 600/16 |
| 2010/0211127 A1* | 8/2010 | Eerden | A61H 31/005 607/5 |

(Continued)

OTHER PUBLICATIONS

International Search Report and Written Opinion, PCT/US2014/041089, dated Oct. 31, 2014, 12 pages.

(Continued)

*Primary Examiner* — Roy Y Yi
*Assistant Examiner* — Jeffrey Aiello
(74) *Attorney, Agent, or Firm* — The Webb Law Firm

(57) ABSTRACT

A computer-implemented method for providing summary information for lifesaving activities is disclosed.

22 Claims, 14 Drawing Sheets

(56) References Cited

U.S. PATENT DOCUMENTS

| | | | |
|---|---|---|---|
| 2012/0123224 A1 | 5/2012 | Packer et al. | |
| 2012/0203147 A1* | 8/2012 | Lurie | A61K 31/21 |
| | | | 601/41 |
| 2012/0330199 A1* | 12/2012 | Lurie | A61H 9/0078 |
| | | | 601/41 |
| 2012/0330200 A1* | 12/2012 | Voss | A61H 31/004 |
| | | | 601/41 |
| 2013/0331719 A1* | 12/2013 | Freeman | A61B 5/046 |
| | | | 600/518 |
| 2014/0100486 A1* | 4/2014 | Alberts | A61B 5/1106 |
| | | | 600/595 |
| 2014/0201627 A1* | 7/2014 | Freeman | G06F 3/04847 |
| | | | 715/704 |
| 2014/0342331 A1* | 11/2014 | Freeman | G09B 23/288 |
| | | | 434/265 |
| 2015/0065815 A1* | 3/2015 | Najarian | A61B 5/486 |
| | | | 600/301 |
| 2015/0150468 A1* | 6/2015 | Ong | G06F 19/345 |
| | | | 600/483 |

OTHER PUBLICATIONS

Lynch, Cheryl, et al., "Functional Electrical Stimulation," IEEE Control Systems Magazine, Apr. 2008, pp. 40-50.

* cited by examiner

Overall Performance

| Depth | Rate | Compression Fraction | Pre-shock Pause | Post-shock Pause | Perfusion Index |
|---|---|---|---|---|---|
| 1.8 in | 118 cpm | 73% | 2.5 sec | 3.1 sec | 91% |
| [1.5-3.0 in] | [100-120 cpm] | [75%+] | [<3 sec] | [<6 sec] | [90%+] |

Minute-by-Minute CPR

| CPR Interval | Depth | Rate | Compression Fraction | Pre-shock Pause | Post-shock Pause | Perfusion Index | Defibrillation | Rosc? |
|---|---|---|---|---|---|---|---|---|
| 1 | 1.9 in | 120 cpm | 78% | 2.7 | 3.0 | 90% | | |
| 2 | 1.2 in | 118 cpm | 70% | 2.5 | 3.3 | 94% | | |
| 3 | 1.5 in | 116 cpm | 70% | 2.3 | 3.8 | 86% | | |
| Current | 3.2 in | 110 cpm | | | | | | |

FIG. 2A

RESCUE PERFORMANCE METRICS FOR CPR AND TRAUMATIC BRAIN INJURY

CLAIM OF PRIORITY

This application claims priority under 35 USC § 119(e) to U.S. Patent Application Ser. No. 61/833,296, filed on Jun. 10, 2013, the entire contents of which are hereby incorporated by reference.

TECHNICAL FIELD

This document relates to computer-based systems and techniques for analyzing performance of a rescuer in performing CPR and other related lifesaving techniques.

BACKGROUND

Sudden cardiac arrest (colloquially "heart attack") is a regular killer. The best treatment for cardiac arrest is quick and competent chest compressions to keep blood flowing through a victim's heart. Generally, every minute of delay in treating a cardiac arrest victim lowers the chance of survival by about ten percent. As a result, the ability to provide CPR in a competent manner can be a very important personal skill, and is particularly important for professional healthcare workers such as emergency medical technicians (EMTs).

Various CPR feedback devices are available that indicate to a rescuer whether they are performing CPR chest compressions at an appropriate rate and an appropriate depth of compression, such as dictated by American Heart Association (AHA) guidelines. For example, the PocketCPR application for iPhones and iPods may be used for practicing CPR, such as on a dummy or foam block, and may indicate whether a recent series of compressions was performed at the proper rate and proper depth. Similarly, the ZOLL Medical CPR D-Padz are defibrillation pads that connect to a defibrillator and include an accelerometer that can be used to compute the depth and rate of chest compressions on the victim so that the defibrillator can indicate via recorded voice prompts that a rescuer should be instructed, for example, to "press harder" if the unit determines that the depth of compression is too shallow.

Professional responders such as EMTs may also receive after-the-fact feedback via processes sometimes referred to as code reviews. In particular, data from a patient monitor (which may be incorporated into a defibrillator) may be saved and may then be loaded into a computer where the responder and a supervisor may review the data and then may discuss where the responder made errors or performed well, and what the responder can do to improve his or her performance. Sometimes these code reviews may occur well after the event, after the responder has largely forgotten the key aspects of the event.

SUMMARY

This document describes systems and techniques that may be used to gather information regarding the performance of CPR and other lifesaving techniques on a patient such as treatment of a traumatic brain injury, and may provide one or more reports at a number of different locations for such performance. For example, data may be gathered for direct primary measurements of aspects of CPR, such as depth and frequency of compressions. That data may be reported immediately on a patient monitor while the rescuer is performing CPR. Additionally, derivative indicators of rescuer performance may also be determined for secondary indications of the performance of the CPR that are derived from two or more of the primary indicators. Such secondary indications may also be displayed to the rescuer while he or she is performing the CPR. In addition, while certain measurements may be reported for actions within a sub-set of a CPR cycle or interval, other measurements may be reported for a period across an entire interval, so that a rescuer can compare his or her current performance to performance for prior CPR intervals—where a CPR interval is the period for a complete cycle of monitoring, defibrillating, and providing a series of chest compressions to a patient, such as defined by the 2010 AHA CPR Guidelines.

Such information, and in particular the secondary derived information, may be used to generate a form of report card for the rescuer, where data for the report card may be displayed in real-time on a patient monitor along with the raw data (e.g., for rate and depth of compressions) used to generate the report card. As a result, the rescuer may receive greater motivation to improve his or her performance, given that he or she is being shown parameters on which his or her performance will ultimately be reviewed. In some examples, the report card can include an additional weighted score that factors in event specific factors that may have influenced the quality of the CPR or treatment. For example, in one case a rescuer may have a low compression fraction (percent of time in CPR) because of challenges at the scene (e.g. disruptive family members, lots of stairs, narrow hallways, etc) which make it impossible to perform high quality CPR. Additionally, information about the patient can be associated with the report card. For example, CPR quality may be affected by patient size (deeper compressions for larger patient, shallow compressions for small and fragile patient) and thus information about the patient may be helpful in understanding the CPR performance. In some additional aspects, after information about the patient is entered, the CPR or treatment can be re-scored to take into account this information.

In certain aspects, a computer-implemented method includes sensing one or more parameters associated with performance of CPR performed on a victim by a rescuer, identifying a timing interval over which performance is to be analyzed and gathering data from the sensing of the one or more parameters during the time interval, generating, from analysis of the parameters, a CPR performance metric that condenses data sensed for the one or more parameters into a single metric indicative of overall performance of the CPR over the identified interval, generating, from analysis of the parameters, a weighted CPR performance metric that condenses data sensed for the one or more parameters into a single metric indicative of overall performance of the CPR over the identified interval with the metric being weighted based on one or more event specific factors associated with the particular rescue attempt, and providing, for display to a user, a visual summary including the CPR performance metric and the weighted CPR performance metric.

Embodiments can include one or more of the following.

The event specific factors can include one or more of duration of CPR administration by the rescuer and a number of defibrillation shocks administered during the duration of CPR administration by the rescuer.

Providing the visual summary can include providing a graphical display of CPR compression rate, CPR compression depth and CPR fraction during the identified interval.

Providing the visual summary can include providing per-parameter metrics with each per-parameter metric condensing data for the parameter to provide a single metric indicative of the CPR quality for that parameter and providing per-parameter weighted metrics with each per-parameter weighted metric condensing data for the parameter.

Providing, for display to a user, a visual summary including the CPR performance metric can include providing the visual summary within one minute of cessation of the CPR by the rescuer.

Providing the visual summary for display can include wirelessly transmitting data about the one or more activities from a device that senses the one or more activities to a remote device having a visual display device display.

The CPR performance metric and the weighted CPR performance metric can each be a score that indicates by one alpha-numeric indicator, a quality level with which one or more CPR related activities were performed.

Generating the CPR performance metric can include generating a single data value from information received from measurement of two or more distinct actions performed on the victim.

Generating the CPR performance metric can include generating a single data value from information about CPR depth, CPR compression rate, and CPR fraction and generating the weighted CPR performance metric comprises generating a single data value from information about CPR depth, CPR compression rate, and CPR fraction that is weighted based on one or more of a duration of CPR administration by the rescuer and a number of defibrillation shocks administered during the duration of CPR administration by the rescuer.

The method can also include receiving information associated with the CPR performance; and
re-generating the CPR performance metric and the weighted CPR performance metric based on updated protocol information selected based on the received information.

In some aspects, a computer-implemented method includes sensing one or more parameters associated with treatment of a traumatic brain injury victim by a rescuer, identifying a timing interval over which performance is to be analyzed and gathering data from the sensing of the one or more parameters during the time interval, generating, from analysis of the parameters, per-parameter metrics with each per-parameter metric condensing data for the parameter to provide a single metric indicative of the treatment quality for that parameter, and providing, for display to a user, a visual summary including the per-parameter metrics.

Embodiments can include one or more of the following.
The method can also include receiving information associated with the treatment and re-generating the per-parameter metrics based on updated protocol information selected based on the received information.

Providing the per-parameter metrics can include providing a display of metrics associated with systolic blood pressure, end tidal carbon dioxide (EtC02), and blood oxygen saturation (Sp02).

Providing, for display to a user, a visual summary including the per-parameter metrics can include providing the visual summary within one minute of cessation of the CPR by the rescuer.

Providing the visual summary for display can include wirelessly transmitting data about the one or more activities from a device that senses the one or more activities to a remote device having a visual display device display.

The per-parameter metrics can each be a score that indicates by one alpha-numeric indicator, a quality level with which one or more treatment activities were performed.

The method can also include generating an overall traumatic brain injury treatment metric that condenses data sensed for the one or more parameters into a single metric indicative of overall performance of the treatment over the identified interval.

The details of one or more embodiments are set forth in the accompanying drawings and the description below. Other features and advantages will be apparent from the description and drawings, and from the claims.

DESCRIPTION OF DRAWINGS

FIGS. 2A and 2B are screen shots of a tablet device showing a summary of rescuer performance in a CPR setting.

Like reference symbols in the various drawings indicate like elements.

DETAILED DESCRIPTION

This detailed description discusses examples of implementations that may be employed in capturing data from a rescuer performing CPR and other related activities on a patient or victim (the terms are used interchangeably here to indicate a person who is the subject of intended or actual CPR and related treatment, or other medical treatment). The data may include both primary data that directly measures a parameter of an action performed on the patient, as well as secondary data that is derived from multiple pieces of the primary data. Also, the data may include real-time data for portions of a current CPR interval, and past data for prior CPR intervals. For example, a device may show the depth and rate of compression for the last compression (e.g., for depth) or last few chest compressions (e.g., for rate) performed by a rescuer. Adjacent that representation, the device may show the average rate and depth of compressions performed for each of the prior several CPR intervals. In such a manner, the rescuer can quickly see how they are doing and can adjust their performance accordingly, and then receive immediate feedback on whether their adjustments have been effective.

Figure 1A:
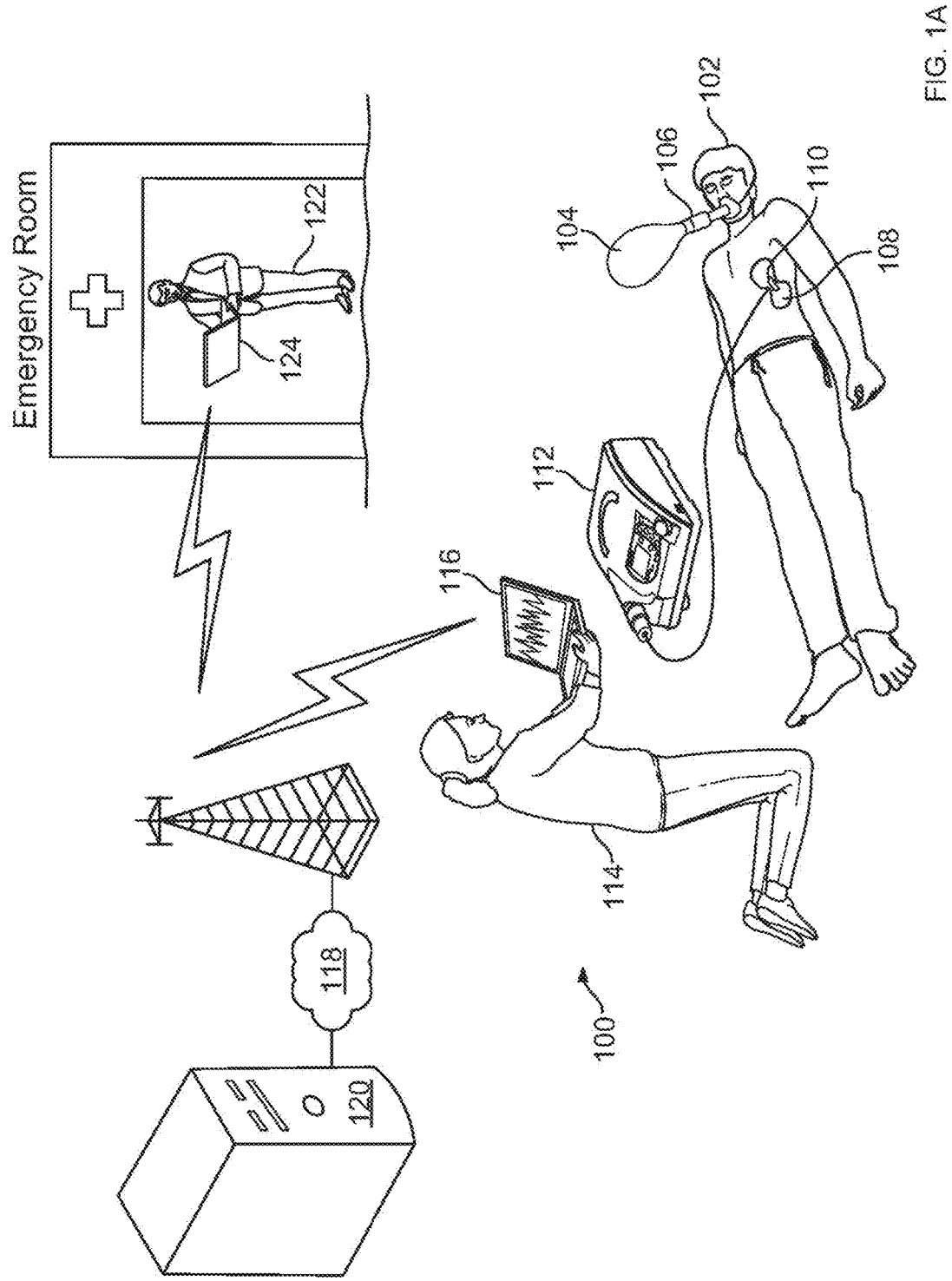
FIG. 1A shows a system for responding to an emergency medical condition.

FIG. 1 shows a system 100 for responding to an emergency medical condition of a victim 102. In general, system 100 includes various portable devices for monitoring on-site care given to a victim of an emergency situation, such as a victim 102 suffering from sudden cardiac arrest or a victim 102 at the scene of a traffic accident. The various devices may be provided by emergency medical technicians who arrive at the scene and who provide care for the victim 102, such as emergency medical technician 114. In this example, the emergency medical technician 114 has deployed several devices and is providing care to the victim 102. Although not shown, one or more other emergency medical technicians may be assisting and working in coordination with emergency medical technician 114 according to a defined protocol and training.

The emergency medical technician 114 in this example is interacting with a computing device in the form of a touchscreen tablet 116. The tablet 116 may include a graphical display by which to report information to the emergency medical technician 114, and may have an input mechanism such as a keyboard or a touchscreen by which the emergency medical technician 114 may enter data into the system 100. The tablet 116 may also include a wireless transceiver for communicating with a wireless network, such as a 3G or 4G chipset that permits long distance communication over cellular data networks, and further through the internet.

Separately, a portable defibrillator 112 is shown in a deployed state and is connected to the victim 102. In addition to providing defibrillation, the defibrillator 112 may serve as a patient monitor via a variety of sensors or sensor packages. For example, as shown here, electrodes 108 have been applied to the bare chest of the victim 102 and have been connected to the defibrillator 112, so that electrical shocking pulses may be provided to the electrodes in an effort to defibrillate the victim 102, and electrocardiogram (ECG) signals may be read from the victim 102. The defibrillator 112 may take a variety of forms, such as the ZOLL MEDICAL R Series, E Series, or M Series defibrillators.

The assembly for the electrodes 108 includes a center portion at which an accelerometer assembly 110 is mounted. The accelerometer assembly 110 may include a housing inside which is mounted an accelerometer sensor configuration. The accelerometer assembly 110 may be positioned in a location where a rescuer is to place the palms of their hands when performing cardio pulmonary resuscitation (CPR) chest compressions on the victim 102. As a result, the accelerometer assembly 110 may move with the victim's 102 chest and the rescuer's hands, and acceleration of such movement may be double-integrated to identify a vertical displacement of such motion (i.e., to compute the displacement of the victim's breastbone for comparison to American Heart Association (AHA) guidelines).

The defibrillator 112 may, in response to receiving such information from the accelerometer assembly 112, provide feedback in a conventional and known manner to a rescuer, such as emergency medical technician 114. For example, the defibrillator 112 may generate a metronome to pace such a user in providing chest compressions. In addition, or alternatively, the defibrillator 112 may provide verbal instructions to the rescuer, such as by telling the rescuer that they are providing compressions too quickly or too slowly, or are pushing too hard or too soft, so as to encourage the rescuer to change their technique to bring it more in line with proper protocol—where the proper protocol may be a protocol generated by the system, but that is inconsistent with any published protocols. In addition, similar feedback may be provided visually on a screen of the defibrillator, such as by showing a bar graph or number that indicates depth and another that indicates rate, with appropriate mechanisms to indicate whether the depth and rate or adequate, too low, or too high.

The defibrillator 112 may communicate through a short range wireless data connection with the tablet 116, such as using BLUETOOTH technology. The defibrillator 112 can provide to the tablet 116 status information, such as information received through the electrode assembly 108, including ECG information for the victim 102. Also, the defibrillator 112 can send information about the performance of chest compressions, such as depth and rate information for the chest compressions. The tablet 116 may display such information (and also other information, such as information from the defibrillator regarding ETCO2 and SPO2) graphically for the emergency medical technician 114, and may also receive inputs from the emergency medical technician 114 to control the operation of the various mechanisms at an emergency site. For example, the emergency medical technician 114 may use the tablet 116 to change the manner in which the defibrillator 112 operates, such as by changing a charging voltage for the defibrillator 112.

Where described below, the processing and display of data may occur on the defibrillator 112, the tablet 116, or on both. For example, the defibrillator 112 may include a display that matches that of the tablet 116, and the two may thus show matching data. In contrast, the defibrillator 112 may have a more limited display than does the tablet 116, and might show only basic information about the technician's performance, while the tablet 116 may show more complete information such as secondary historic information. Also, the processing of primary information to obtain secondary information may be performed by the defibrillator 112, the tablet 116, or a combination of the two, and the two devices may communicate back and forth in various manners to provide to each other information they have received or processed, or to relay commands provided to them by the technician 114.

Another electronic mechanism, in the form of a ventilation bag 104, is shown sealed around the mouth of the victim 102. The ventilation bag 104 may, for the most part, take a familiar form, and may include a flexible body structure that a rescuer may squeeze periodically to provide ventilation on the victim 102 when the victim 102 is not breathing sufficiently on his or her own.

Provided with the ventilation bag 104 is an airflow sensor 106. The airflow sensor 106 is located in a neck of the ventilation bag 104 near the mouthpiece or mask of the ventilation bag 104. The airflow sensor 106 may be configured to monitor the flow of air into and out of the patient's mouth, so as to identify a rate at which ventilation is occurring with the victim. In addition, in certain implementations, the airflow sensor 106 may be arranged to monitor a volume of airflow into and out of the victim 102.

In this example, the airflow sensor 106 is joined to a short-range wireless data transmitter or transceiver, such as a mechanism communicating via BLUETOOTH technology. As such, the airflow sensor 106 may communicate with the tablet 116 in a manner similar to the communication of the defibrillator 112 with the tablet 116. For example, the airflow sensor 106 may report information that enables the computation of a rate of ventilation, and in some circumstances a volume of ventilation, that is being provided to the patient. The tablet 116, for example, may determine an appropriate provision of ventilation and compare it to the level of ventilation that the victim is receiving, and may provide feedback for a rescuer, either directly such as by showing the feedback on a screen of the tablet 116 or playing the feedback through an audio system of the tablet 116, or indirectly, by causing defibrillator 112 or airflow sensor 106 to provide such feedback. For example, defibrillator 112 or airflow sensor 106 may provide a metronome or verbal feedback telling a rescuer to squeeze the ventilation bag 104 harder or softer, or faster or slower. Also, the system 100 may provide the rescuer was an audible cue each time that the bag is to be squeezed and ventilation is to be provided to the victim 102.

Such feedback may occur in a variety of manners. For example, the feedback may be played on built-in loudspeakers mounted in any of tablet 116, defibrillator 112, or airflow sensor 106. Alternatively, or in addition, visual notifications may be provided on any combination of such units. Also, feedback may be provided to wireless headsets (or other form of personal device, such as a smartphone or similar device that each rescuer may use to obtain information and to enter data, and which may communicate wirelessly over a general network (e.g., WiFi or 3G/4G) or a small area network (e.g., BLUETOOTH) that are worn by each rescuer, and two channels of communication may be maintained, so that each rescuer receives instructions specific to their role, where one may have a role of operating the defibrillator 112, and the other may have the role of operating the ventilation bag 104. In this manner, the two rescuers may avoid being accidentally prompted, distracted, or confused by instructions that are not relevant to them.

A central server system 120 may communicate with the tablet 116 or other devices at the rescue scene over a wireless network and a network 118, which may include portions of the Internet (where data may be appropriately encrypted to protect privacy). The central server system 120 may be part of a larger system for a healthcare organization in which medical records are kept for various patients in the system. Information about the victim 102 may then be associated with an identification number or other identifier, and stored by the central server system 120 for later access. Where an identity of the victim 102 can be determined, the information may be stored with a pre-existing electronic medical record (EMR) for that victim 102. When the identity of the victim 102 cannot be determined, the information may be stored with a temporary identification number or identifier, which may be tied in the system to the particular rescue crew so that it may be conveniently located by other users of the system.

Information that is stored for a rescue incident may also include an identifier for the technician 114 and any other technician that participated in the rescue. Using such identifiers, the server system 120 may later be queried so as to deliver data for all incidents that the particular technicians have been involved in. The tablet 116 or defibrillator 114 may include mechanisms so that the technicians can identify themselves and thus have their identifier stored with the information. For example, the technicians may be required to log in with the tablet 116 when their shift starts, so that all information subsequently obtained by the tablet 116 or components in communication with the tablet may be correlated to the identifier. Such logging in may require the entry of a user name and password, or may involve biometric identification, such as by the pressing or swiping of a technician's fingertip on a fingerprint reader that is built into the tablet 116.

The information that is stored may be relevant information needed to determine the current status of the victim 102 and the care that has been provided to the victim 102 up to a certain point in time. For example, vital signs of the victim 102 may be constantly updated at the central server system 120 as additional information is received from the tablet 116 (e.g., via the defibrillator 114). Also, ECG data for the victim 102 may be uploaded to the central server system 120. Moreover, information about drugs provided to the victim may be stored. In addition, information from a dispatch center may also be stored on the central server system 120 and accessed by various users such as rescuers. For example, a time at which a call came in may be stored, and rescuers (either manually or automatically through their portable computing devices) can use that time to determine a protocol for treating the patient (e.g., ventilation or chest compression needs may change depending on how long the victim has been in need of treatment).

Other users may then access the data in the central server system 120. For example, as shown here, an emergency room physician 122 is operating his or her own tablet 124 that communicates wirelessly, such as over a cellular data network. The physician 122 may have been notified that victim 102 will be arriving at the emergency room, and, in preparation, may be getting up-to-speed regarding the condition of the victim 102, and determining a best course of action to take as soon as the victim 102 arrives at the emergency room. As such, the physician 122 may review the data from central server system 120. In addition, the physician 122 may communicate by text, verbally, or in other manners with emergency medical technician 114. In doing so, the physician 122 may ask questions of the emergency medical technician 114 so that the physician 122 is better prepared when the victim 102 arrives at the emergency room. The physician 122 may also provide input to the emergency medical technician 114, such as by describing care that the emergency medical technician 114 should provide to the victim 102, such as in an ambulance on the way to the emergency room, so that emergency room personnel do not have to spend time performing such actions. Also, physicians could see aspects of a currently-operating protocol on the system (e.g., an AHA CPR protocol), and could act to override the protocol, with or without the rescuers needing to know that such a change in the protocol has been made (e.g., their devices will just start instructing them according to the parameters for the manually-revised protocol).

Where the published protocol is organized in a flowchart form, the flowchart may be displayed to a rescuer or a physician, and such user may drag portions of the flowchart to reorder the protocol. Alternatively, the user could tap a block in the flowchart in order to have parameters for that block displayed, so that the user can change such parameters (e.g., ventilation volume or time between ventilations). Data describing such an edited protocol may then be saved with other information about an incident so that later users may review it, and a user may save reordered protocols so that they can be employed more easily and quickly in the future.

In this manner, the system 100 permits various portable electronic devices to communicate with each other so as to coordinate care that is provided to a victim 102. In addition, the system 100 allows the technician 114 and others to see raw real-time data and derived real-time or historical data about a rescue attempt. Such data may be arranged so that a technician can immediately see whether his or her performance is matching or has matched agreed-upon standard, and can quickly adjust his or her performance while the incident is still going on. In addition, such information may be aggregated across multiple incidents for a particular rescuer, and across multiple incidents for multiple rescuers so as to be able to provide more broad-based report cards for performance, and to permit more general modification of future performance (e.g., for a rescuer who regularly underperfuses victims).

Each device in the system 100 may sense information about the care provided to the victim 102, and/or may provide instructions or may store data about such care. As a result, the system 100 may provide improved care for the victim 102 by better integrating and coordinating each form of the care that the victim 102 receives. The victim 102 made thus receive improved care and an improved chance of obtaining a positive outcome from an event.

In certain instances, a condition of a victim that is used to generate a protocol for treatment of the victim may be based on on-site observations made by a rescuer, by information in an EMR for the victim, or both. For example, a determination from an EMR that a victim is taking a particular drug may result in a change in protocol for ventilation rate. Likewise, an observation by a rescuer that the victim has suffered a head injury on site may also affect the protocol for ventilation rate. The two factors may also be considered together to determine yet a more refined ventilation rate for which a rescuer will be instructed to provide to the victim. Also, the real-time feedback that is provided to a technician 114 may be automatically altered in response to identifying such special cases in an EMR or in information entered by the technician 114 (e.g., after a conscious victim has provided the information to the technician 114).

Thus, in operation, a two-person rescue team may arrive at a scene. One member of the team may set up and attach a defibrillator/monitor to a victim, and do the same with a ventilation bag assembly. The other member may begin an examination of the victim and may enter information obtained from the examination into a portable computing device such as a general tablet computer (e.g., an iPad or netbook). In some situations, the second rescuer may be able to verbally interview the victim, at least initially, so as to determine whether the victim is lucid, what drugs the victim may be taking, and the like. The second rescuer could also make visual observations (e.g., types of trauma to the victim) and record those in the computing device. Moreover, one of the rescuers may obtain vital sign information for the victim, and such information may be entered manually into the computing device or automatically, such as through wireless links from a blood pressure cuff, or other relevant medical device.

The computing device, using all of the entered information, may then generate a protocol for treating the victim. Such a generating may occur by selecting from among a plurality of available protocols by plugging the observations into a protocol selector. The generation may also be more dynamic, and may depends on a series of heuristics that use the observations as inputs, and generate a protocol (which may be made up of one or more sub-protocols) as an output. Moreover, a lookup table may be consulted, where the table may define correlations between particular observed patient conditions or physical parameters, and a particular feature of a treatment protocol.

The computing device may also submit the observation information over a network such as the internet, and a protocol may be generated by a central computer server system and then automatically downloaded to, and implemented by, the portable computing device. Such an approach may have the benefit of being able to easily update and modify protocol-generation rules.

The computing device may then receive information about the performance by the rescuers, such as from wired or wireless transmitters on a defibrillator, an assisted ventilation unit, or other medical device (e.g., blood pressure reader). The computing device may provide feedback or coaching when the performance falls out of line with a defined protocol, or may provide feedback to maintain the performance in line with the protocol. In providing the feedback, the computing device or the defibrillator/monitor may generate a number of derived parameters from measure parameters of the victim, and both the measured parameters and the more comprehensive derived parameters may be reported visually or audibly by the computing device, the defibrillator/monitor, or both. Also, the computing device may update the protocol as care is being provided to the victim. For example, the rate of required ventilation or chest compressions may change as a function of time. Also, if one of the rescuers attaches an oxygen source to a ventilation assembly (as sensed, e.g., by a switch where the connection occurs, by a manual rescuer input to the system, or by sensors in the assisted ventilation system), the rate of required ventilation may change. Other changes in the patient condition, such as changes in measured levels of ETCO2 or SpO2, can lead to the computing device generating a revised protocol and providing feedback to the rescuers so that they adapt to the revised protocol (sometimes without consciously knowing that the protocol has been revised). In some additional examples, the rescuer can manually change the protocol. For example, the rescuer could indicate that the patient has achieved ROSC and the protocol would automatically switch to a post-resuscitative care protocol. Further, in some examples, the change of protocol could be automated, for example, the identification of ROSC could be automated (e.g., automatically determined by a computing device based on a jump in ETCO2 and/or presence of spo2 waveform), which the rescuer would simply need to confirm. If the patient rearrests, and chest compressions resume, the protocol would automatically return to cardiac resuscitation.

Figure 1B:
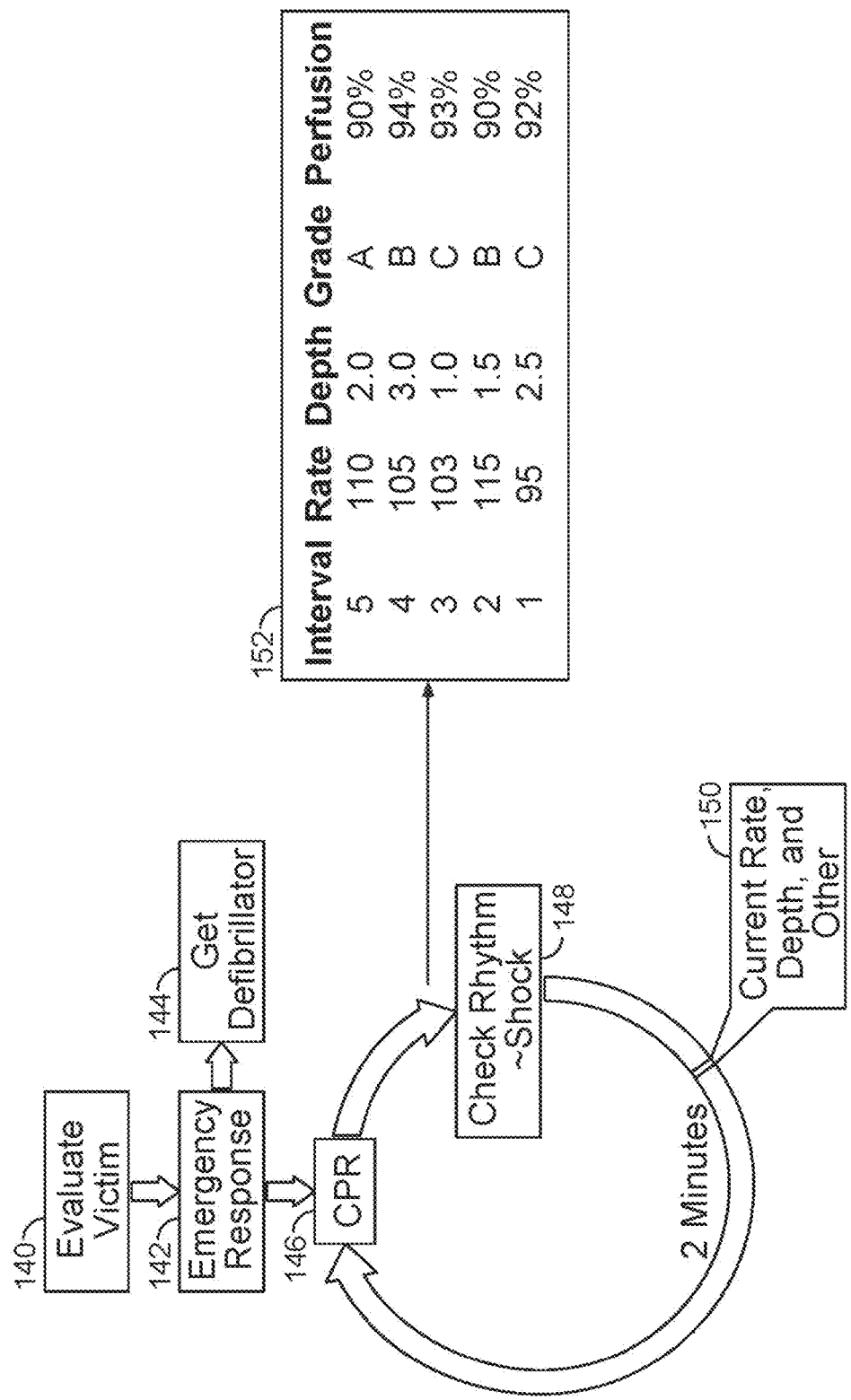
FIG. 1B is a flow diagram of a CPR data acquisition process.

FIG. 1B is a flow diagram of a CPR data acquisition process. In general, the data acquisition occurs in parallel with performance of CPR according to the 2010 American Heart Association Guidelines for Cardiopulmonary Resuscitation and Emergency Cardiovascular Care. Data acquisition in this example occurs in real-time throughout the provision of CPR to a victim, and such real-time data may be continuously updated and displayed to rescuers or others. Also, certain secondary information may be generated from the real-time information, either periodically such as at the end of each CPR interval in the cycles, or at the end of a rescue incident (where an incident is an entire attempt to rescue a victim, from the beginning of data collection to the time a patient monitor is removed from a patient, the patient leaves the scene of the incident, or another rescuer or group of rescuers takes over).

According to the CPR guidelines, the process begins at box 140, where a rescuer endeavors to evaluate a victim. Such evaluation may occur by familiar mechanisms, such as by determining whether the victim is breathing, responsive, or has a pulse. If a problem with the victim is determined, the rescuer begins an emergency response at box 142. For example, the rescuer may cause an emergency response team to be called to the scene and may get a defibrillator 144 or cause another person to get a defibrillator if the victim appears to suffer from sudden cardiac arrest or a similar problem.

Having performed such actions, the rescuer may begin performing cardio pulmonary resuscitation (CPR) on the victim at box 146. According to protocol, CPR involves a cyclical process that is repeated every two minutes, as indicated by the circular arrow in the figure. At the beginning of each cycle, a defibrillator that has had leads attached to the victim may analyze the victim, such as by analyzing an ECG reading for the victim or other information to determine whether the victim has a shockable rhythm. Techniques for performing such analysis are well-known and the particular technique that is used here is not critical. If a shockable rhythm is determined to be present, a shock may be delivered as shown by box 148. For example, the defibrillator may provide a display to a rescuer or may speak words to the rescuer indicating that a shock should be delivered. The rescuer may then press a button on the defibrillator to cause a shock to be delivered, after all people around the victim have moved away from the victim.

The rescuer may then perform chest compressions on the victim for the remainder of the cycle or interval. After a predetermined time period of providing chest compressions, or during the chest compressions, the defibrillator may again analyze the victim's condition to determine whether they have a shockable rhythm. For example, the defibrillator may include componentry for filtering out CPR artifacts from chest compressions as compared to an ECG signal, and may perform the analysis on the filtered signal.

Box 150 is shown along the loop of the CPR cycle to indicate a current time in the cycle. In particular, the box 150 indicates that the defibrillator or another device may, at the current point in time, be computing and displaying certain parameters regarding the care that is being provided to the victim. Certain of those parameters may be initial or primary parameters in that they are direct representations of values read from the patient. Such parameters may include depth and rate of chest compressions provided to the victim. Other of the reported parameters may be secondary parameters in that they are derived from the initial parameters, either from one or a multiple of different initial parameters. For example, certain values may be computed from a combination of the compression rate and the compression depth. Also more general composite values may be generated, such as a letter or number grade that indicates how the rescuer is currently performing. In some examples, the general composite value can be based in part on multiple variables including one or more of compression rate, compression depth, compression release, and compression fraction (e.g., the percent of time in compressions)

Box 152 represents values that are generated periodically, such as with each cycle of a CPR interval in a particular location in the interval, or at the end of an incident. The values that are generated may include, for example, average values for particular primary parameters over a period of an interval. For example, the average rate and depth over an interval may be computed at the end of each interval and may be saved in a database such as in a manner shown by box 152. Additional data such as compression fraction and compression release velocity can be computed at the end of each interval and may be saved in the database. The compression release velocity can be either an actual release velocity or a categorical indicator of release such as— excellent, good, poor—to allow simpler analysis.

Also, the saved parameters may include derived or secondary parameters that are computed from initial parameters, such as from average values of initial parameters, or by combining multiple initial parameters from throughout an interval, and then averaging the combination. In this example, a perfusion percentage is given as one example of a secondary or derived parameter, and letter grades for each interval are also secondary or derived parameters. In some examples, if multiple rescuers are participating in the rescue, the data stored in the database for each CPR cycle can include an indication of which rescuer performed compressions in each interval (e.g., based on an assigned anonymous ID).

In this manner, a performance reporting approach may be implemented in coordination with standard CPR techniques so as to capture and report information that is particularly relevant to a rescuer or to a party after the fact of a rescue. The information may include basic measurements from the performance of CPR on a patient, and may also include derived values that may provide a model or compelling or understandable representation of the rescuers performance. For example, the parameter that is displayed to the rescuer may be similar to or the same as a parameter on which the rescuers performance will be judged by a later review work of an incident as part of the code review. The rescuer may thus be more responsive to such a displayed parameter if the rescuer is performing poorly, than the rescuer would be in response to simple values of depth and rate of compressions. As a result, the rescuer may be more likely to change his or her behavior in a positive manner so as to improve the care that is provided to a patient or victim.

The monitoring and feedback provided by such a process may also be affected by basic configuration data obtained by the system. For example, before monitoring by the system begins, a process may have gathered certain data to aid in the monitoring. For example, as a rescuer sets up a defibrillator and hooks it to a victim, the defibrillator may ask the rescuer (on a display or via a spoken request) whether the rescuer is alone or is being aided, and might also ask how many additional rescuers are available. If the rescuer indicates that he or she is alone, then the system may follow a branch of programming that does not recommend switching of rescuers, but might more aggressively provide feedback in order to overcome the extra fatigue a solo rescuer will face. If the rescuer is accompanied, then the system may subsequently indicate when rescuers are to switch roles. The system may also assign a label to each rescuer, such as "Rescuer 1" and "Rescuer 2" or the actual names of the rescuers (which could have been programmed previously, such as for EMTs who use the system frequently, or could be obtained, such as by lay rescuers speaking their names into the device in response to prompts from the device). If there are three or more rescuers, instructions for rotating may be more complex— i.e., involving more than simply an instruction to switch positions, but instead telling each rescuer what component of CPR they should be performing for any particular time period. Additionally, the protocol used to direct the rescue can be changed based on the number of rescuers at the scene. For example, if the rescue begins with a single rescuer and another rescuer arrives subsequently, the additional rescuer can change the protocol to a two rescuer protocol.

A determination about the number of rescuers may also be made inferentially. For example, a ventilation bag may include electronics that report to a defibrillator or other box, and the box may sense that the bag is being deployed or used, or is being used simultaneous with chest compressions being performed, in order to infer that there are at least two rescuers. The defibrillator may adjust its operation accordingly in the manners discussed above in such a situation (e.g. by enabling prompts for rescuers to switch roles).

As for operation of the system during performance of CPR, in certain circumstances, prompts for performing CPR may change the way in which CPR is to be performed in response to indications that there has been a degradation in performance. For example, a protocol by which a user is instructed may change based on such an observation that performance has degraded, so as hit a performance level that the user can better maintain, even if that level is sub-optimal. In particular, prompting of CPR at a sub-optimal level may be provided, as long as that sub-optimal level is better than wholly fatiguing a rescuer.

For example, hemodynamics data has indicated that depth of chest compressions may be more important to victim well-being than is rate of compressions—i.e., it may essentially not matter how fast you are performing compressions if none of those compressions is truly effective. As a result, a system may slow a rate (e.g., a metronome) of prompting compressions and may monitor how the depth of compressions changes in response to the prompted change in rate. Using stored hemodynamic data correlating depths and rates to effectiveness, the system may identify a most-preferred rate that maximizes the hemodynamic effect for a particular rescuer (using, e.g., the well-known Windkessel model or other approach). While such modifications may be made only after sensing that a particular rescuer is fatiguing, they can also be initiated at other points and in response to other criteria, including by making such adjustments throughout a rescue cycle (e.g., the rate of a metronome may be adjusted slightly and essentially continuously, and the combination of depth and rate that is measured from the rescuer may be input in real-time to a formula for computing hemodynamic effect, with subsequent changes in the rate of the metronome being made in an attempt to increase the hemodynamic effect within bounds of safety).

Also, physical data of the rescuer or rescuers may also be monitored while care is being provided to a victim, such as to determine whether the rescuers are tiring and should be prompted in a different manner, or should be instructed to switch out to other rescuers as they fatigue. For example, a rescuer may be outfitted with a pulse oximeter such as one that can be attached to a CPR puck on a victim's chest and into which the rescuer can place one or more fingers. The readings of the rescuer's blood oxygen level and pulse rate may be used to determine that the rescuer is fatiguing and will not be able to continue performance at a current level for very long. As a result, a medical device can cause the rescuer to switch places with another rescuer, may provide encouragement to the rescuer, or may reduce the rate or severity with which the rescuer is providing care so as to maximize the work the rescuer can do, even if it is below what would otherwise be considered an optimum level of care.

Thus, these techniques may be used to identify rescuer performance, including indications of fatigue while providing such performance, for review by the rescuers or other at various points in time. For example, a medical device may immediately monitor the performance to provide feedback or adjust the manner in which it provides feedback so as to maintain a best level of performance over the length of a rescue operation, including by instructing rescuers to switch places at appropriate times so as to lessen the effect of fatigue. The rescuers themselves may also be provided with information as described above and below so that they may adjust their performance of care on a victim in real-time as they perform the care. Also, care may be reviewed after the fact, such as by rescuers to determine how they can perform better as a team or perhaps to determine that they should increase their physical conditioning to combat fatigue, and also by supervisors.

FIG. 2A is a screen shot of a tablet device showing a summary of rescuer performance in a CPR setting. In general, the screen shot shows roughly the sort of parameters that may be displayed on a tablet computer as feedback for a rescuer at the scene of an accident, or to a physician who is following the performance of care on a victim remotely.

The presentation of information in this example is split into two portions—a top portion that shows averaged performance over an entire incident, and a bottom portion that shows the performance average over each of the last three CPR intervals, with display of current depth and rate displayed immediately under the second portion.

Referring now to particular portions of the display, a rescuer is shown that their average depth of compression in performing CPR has been 1.8 inches for an incident, and that the appropriate range for compression is 1.5 inches to 3.0 inches. Similarly, the rescuer is shown that their average rate of compressions is 118 compressions per minute (CPM), which is within the approved range of 100 to 120 CPM. The approved range for compression fraction is over 75%, but the average for this rescuer is 73%. The fact that the rescuer is outside of the approved range is indicated here by a dashed box around the average value, to draw attention of the rescuer to the fact that improvement is needed in this value. Similarly, values are displayed for the rescuer's delay in pre-shock and post-shock activity and for a perfusion index by the rescuer. The particular values shown here were selected merely to demonstrate how values may be displayed to a rescuer, such as on a defibrillator/monitor, tablet computer, or similar device, and are not meant to represent actual values that would necessarily be displayed in an actual situation.

In the minute-by-minute CPR area of the display, three lines of values are shown, where the values are average values for each of the last three CPR intervals performed on the victim, so they represent approximately the last six minutes of CPR performed on the victim, though perhaps not the entirety of CPR that has been performed on the victim. Again, individual values are provided for each of the intervals, and values that are outside of range are highlighted by a dashed box, though as discussed below, other mechanisms for drawing attention to out-of-range or in-range values may be employed.

Also, two of the values—for depth and rate of compression—are shown according to their current states. Specifically, the last compression performed by the rescuer had 3.2 inches of travel, and the last several compressions were performed at a rate of 110 CPM. Solid boxes are shown around these values to draw particular attention to them for the rescuer, so that the rescuer can quickly see what his or her immediately current performance has been.

Additional guidance may be provided to a viewer of the display, such as to a rescuer, by using color, animation, and sound feedback. For example, any values on the display that are outside a desired range may be displayed in red, while values at the edge of the range may be displayed in yellow, and values inside the range may be displayed in green color. Also, particularly important values may be highlighted by making them blink, wiggle, or shimmer, so as to call a viewer's attention particularly to them. Also, the device may beep or speak recorded instructions when the rescuer needs guidance in returning to approved performance ranges.

The particular arrangement of values on the display here is provided merely as an example of data that may be shown to a rescuer or to a physician while care is being provided to a victim. Other arrangements of information may also be employed. In particular, less information than is shown here may be provided, and may be shown in a smaller portion of the screen, thus leaving room for the display of other information that may be pertinent to a rescuer. One such example is shown in FIG. 2B.

Figure 2B:
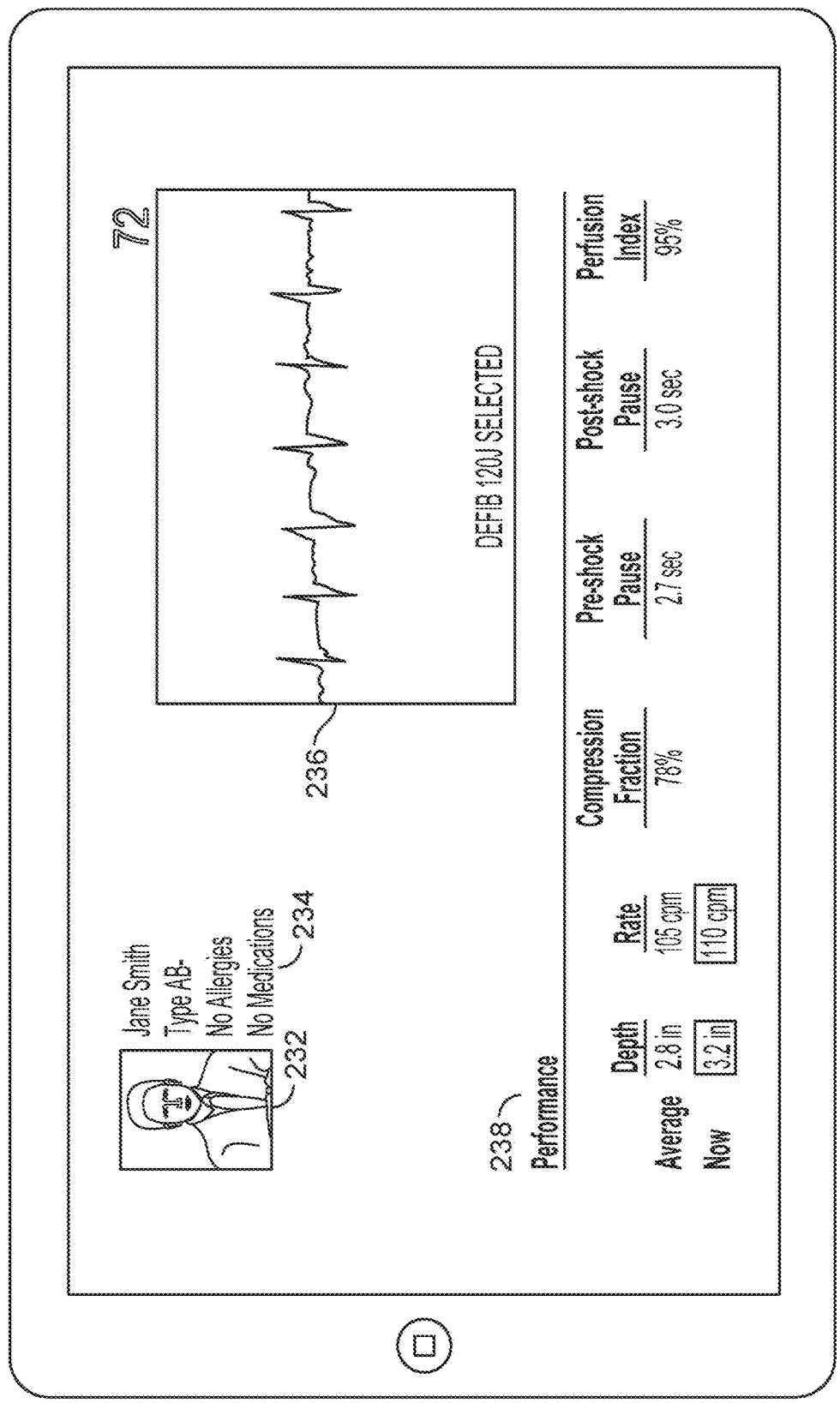

In particular, FIG. 2B shows another screen from a device such as a patient monitor or tablet computer that may be displayed to a rescuer. In this example, a performance area 238 (i.e., an area that rates and reports on the rescuer's performance) takes up a relatively small part of the entire display. The data that is displayed is similar to that displayed in FIG. 2A, but only average values across the entire incident, and immediate values for depth and rate, are displayed. A numerical or alphabetical grade (not shown) may also be provided near this area as a higher level, more summarized, view of the performance.

The relatively small size of the performance area 238 leaves additional room on the display to show other data about a rescue incident. For example, a victim identification area in the upper left corner of the display includes an image 232 of the victim and personal information 234 about the victim. The image 232 may be obtained from a central server system in response to entering identification information for the victim. For example, a driver's license found with the victim may indicate a name of the victim, or a fingerprint may be obtained from a fingerprint reader for the victim, where the fingerprint reader may be incorporated with a blood oxygenation sensor. Such a mechanism for identifying the victim may be used to recover limited medical record information about the victim, such as the blood type, allergies and medications taken by the victim. The image 232 may be displayed so that the rescuer may manually confirm that the patient who is identified by the system is the same person as the victim who is lying front of them (where the victim is unable to identify himself or herself).

An ECG display 236 is also provided in a familiar manner in an area the display 236, showing an ECG trace and may also display warnings or other data such as an indication of the amount to which capacitors on a defibrillator have been charged, and whether they are ready for discharge. Other information that is not shown here may also be provided on the display. For example, countdown timers may be shown to indicate future activities that will need to be performed by the rescue team. As one example, a countdown timer may indicate the amount of time left in a CPR interval. Also a countdown timer may indicate time for another rescuer, such as time for providing ventilation to the patient or victim, or time until a particular drug is to be provided by the rescuers to the victim.

The display may also show content that is typed by a physician at an emergency room, or other similar content. For example, the physician may monitor information like that shown in this figure, and may provide guidance to a rescuer by typing it, similar to an online chat system. In other implementations, a voice connection may be made up with the physician, and instructions from the physician may be heard through the tablet computer, the defibrillator monitor, a BLUETOOTH headset that is provided with data from the tablet or monitor, or through another form of communication device employed by the rescuer.

Using displays like those shown in FIGS. 2A and 2B, a system may provide improved feedback to a rescuer in an emergency situation. The feedback may be provided in a graphical manner that indicates information that is most important to the rescuer, and is thus most likely to be acted upon by a rescuer. Also, the information that is provided may be a form of combined information that provides a higher level view of the rescue operation. For example, a number of different actions or activities that are performed by a rescuer on a victim may be combined using a predetermined formula or algorithm to produce a more general descriptor of the quality of care that is given to the victim. Such automatic combination by the system may relieve a rescuer of having to make such determinations themselves. For example, a particular combination of compression rate and depth, albeit nominally out of range for either rate or depth or both, may be within a desired range when the values for rate and depth are applied against each other, such that out of range values for each variable cancel each other out. Also, where the information is more generalized, it may be more in line with the form of information on which the rescuer will be judged in the performance of their job, so that a rescuer may be more likely to respond to it.

Figure 3:
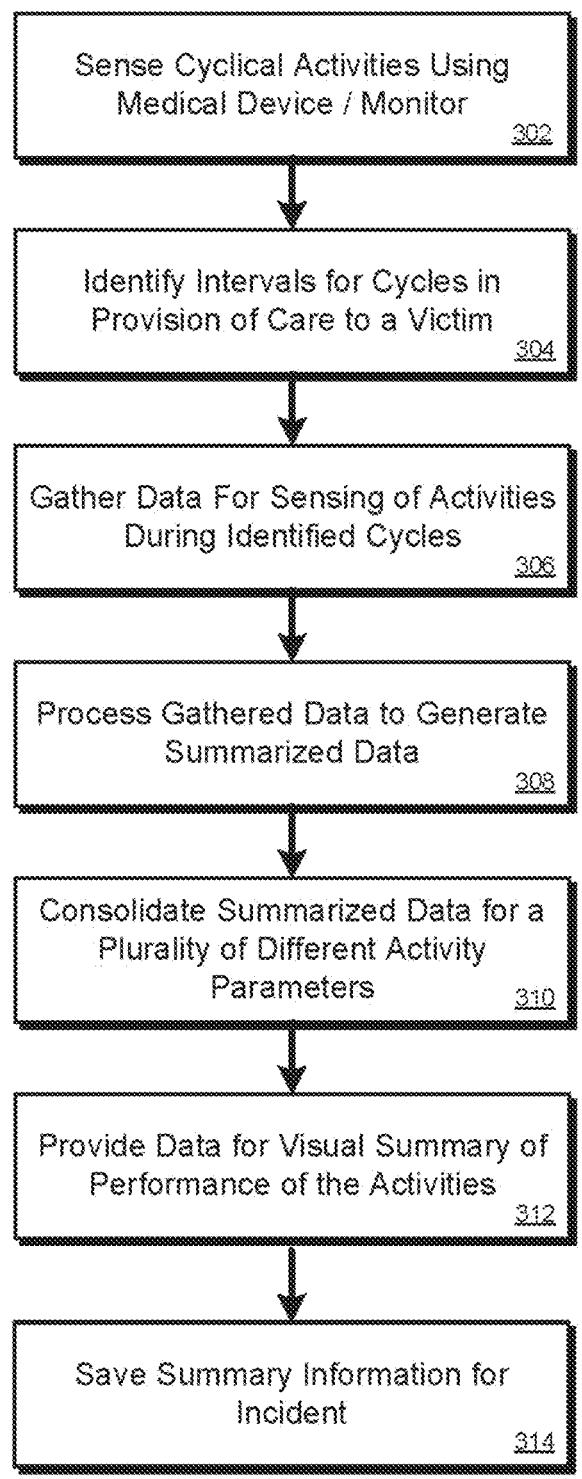
FIG. 3 is a flow chart of a process for capturing user performance data during the provision of CPR.

FIG. 3 is a flow chart of a process for capturing user performance data during the provision of CPR. In general, the process involves receiving raw information from sensors that are connected to a patient monitor, which may be incorporated into a defibrillator as described above, generating derivative data, displaying to a user of the monitor values for the raw data and the derivative data, and also displaying values for real-time measurements and historic measurements. For example, the real-time raw measurements may include depth and rate of compression during CPR that is being performed on a patient who is being monitored. The derived measurements may include a perfusion performance indicator and overall letter or number grade for the performance of the user. The historical measurements may include measurements for portions of, or all of, prior CPR intervals, or for averages from such periods or across multiple intervals.

The process begins at box 302, where a medical device/monitor, such as a defibrillator with built-in capabilities for monitoring motion of chest compressions and ECG signals, among other parameters, senses cyclical activities that are being performed on a patient. Such cyclical activities may include the provision of CPR in a recursive cycle following the 8H a guidelines discussed above, where the cycle involves analyzing a patient such as to determine whether the patient exhibits a shock of all heart rhythm, providing a shock if the patient has such a rhythm, and providing chest compressions to the heart to cause perfusion of blood in and through the heart. The particular activities may generate data from sensors, and the step of sensing the activities may include converting the data to a more usable form, such as by converting a voltage received from an accelerometer into a computed depth of compression for a patient's chest.

At box 304, the process identifies intervals for the cycles in the provision of care to the victim or patient. Thus, for example, the process may identify starting and ending points for each of the CPR intervals and may thereby associate data received between each start point and end point with a particular one of the intervals. Such association of received data with particular intervals may enable the presentation of information about the data to a user in a manner that the information is correlated to the particular intervals in which it was received.

At box 306, data is gathered for sensing activities during the identified cycles. Such data gathering may be continuous during the performance of CPR and other activities on a patient or victim, such that particular ones of the actions described here may be repeated over and over until a rescuer terminates a monitoring described here. As the data is gathered, it may receive a first level processing, such as described above to convert voltages into more usable values such as displacements or accelerations. Similarly, the monitor may change voltages from leads that are attached to the patient into values for an ECG signal that may be easily graphed on the monitor or on another device. Such initially-processed data may then be stored on the device, and copies of some or all of the data may be provided to other devices. For example, the data may be transferred over a short range wireless connection to a device such as a tablet 116 or server 120 in FIG. 1. Such transfer of data may be in batches or may be continuous or substantially continuous. For example, an automatic batch upload of data may be triggered at particular points during treatment of a patient, such as after a rescuer terminates treatment. A proximity sensor may be used to determine that treatment has terminated because the monitor has returned to a vehicle such as ambulance, and such sensing may be used to trigger the batch transfer of data between the monitor and devices in the ambulance, and then further to a separate device such as server 120. In another implementation, the batch transfer may be triggered by a GPS unit in the device sensing that the device is moving above a particular speed, such as 15 mph, and thus concluding that the device has been placed in an ambulance and that its use is complete. In another implementation, the batch transfer may be triggered be data from a dispatch center indicating that the victim has been transferred to an ambulance. Such determination may also be combined with a determination that patient conditions are no longer being received from the various sensors to which the device has been connected. Continuous transfer of data may occur by a variety of mechanisms, such as by caching received and initially-processed data, and then uploading or otherwise transferring the data at close-spaced periods.

In some examples, the analysis of the rescue does not cease at the arrival of the victim to the ambulance. Rather, similar analysis of rescue performance can be applied to separate phases of treatment. For example, once the patient is in transport, it is hard to perform high quality CPR. The device automatically determines when transport begins, and marks the received rescue data as "during transport" on the report card. When a final analysis information is displayed to the rescuer, the analysis can include summary statistics for care on scene only in addition to the entire treatment. Additionally, in some examples, the rescue data can include an indication of arrival at an emergency department, and data gathered after arrival could be excluded from the analysis of the rescue performance. Excluding this data can be useful because in many cases, care is continued for the EMS defibrillator even after arrival at the hospital.

At box 308, the gathered data is processed to generate summarized data, which is a derivative form of the initially gathered data. For example, information about rate and depth of chest compressions may be used along with other information obtained by a system to identify a level of perfusion for a patient. In addition, summaries may be generated for entire CPR intervals or multiple CPR intervals. As one example, particular values that have been captured and recorded for performance of activities on a patient may be aggregated, such as by generating an average value for a CPR interval or an average value across multiple CPR intervals. Thus, for example, a perfusion level for the entire time that a rescuer has been performing CPR on a patient may be computed and may be reported back out to the rescuer.

Also, as shown at box 310, summarized data may be consolidated across a number of activities, such as data relating to chest compressions and data relating to ventilation that can be combined to identify an overall indicator of care that is been provided to the patient. Thus, in such examples, the derivative data may not only be derived from the original data, such as depth of compression, but may also be derived from two separately obtained pieces of original data. Such combining of data sources across multiple activities being performed on the patient may also be used to generate a score or grade for the care provided so far to the patient, so as to indicate manners in which the rescuer can change subsequent care that is given. For example, monitoring of parameters like those discussed in FIGS. 2A and 2B may indicate that a rescuer is too excited or too relaxed in giving their care (e.g., because they are compressing the chest too soft or too hard, or they are acting too quickly or too slowly in certain parts of the CPR interval). In such a situation, a score from −5 to +5 may be assigned, where a score of 0 is perfect, scores farther below 0 indicate that the rescuer needs to be more active in their care, and scores above 0 indicate that the rescuer needs to take a deep breath and relax a bit. Such a score may be displayed in a location on a screen of a monitor, tablet computer or similar computing device. The score or grade for the entire session may also be submitted to a supervisor of the rescuer as part of a post hoc code review of the session. In some examples, in a multi-person rescue, separate scores can be displayed for each rescuer. Displaying scores separately can allow each rescuer to know how to modify their technique.

Such presentation of the raw and derived data is represented by box 312, where a visual summary of the user's performance is displayed. Such display, as discussed above, can be on a monitor, on a tablet, on a separate computer used by another caregiver, or by other mechanisms. The display may take a form, for example, similar to that shown in FIGS. 2A and 2B.

At box 314, summary information for an incident or session is saved. Such a step could take place continuously or semi-continuously throughout an incident or may occur as a batch upload once the incident is over, as discussed above. The information may be saved locally and may also be saved on a more global server system from which supervisors or analysts may access both the raw and derived data. Presentations of the data similar to those shown above may be provided, and a replay may be had of the data that would have been displayed to the rescuer. As a result, the rescuer and an official may step through the session step-by-step, and the official may point out exactly what the rescuer did right and wrong. The presentation may also take a more summarized form, and can roll in data from multiple different incidents, such as all recent incidents of a particular type for a particular rescuer (e.g., all incidents in which a victim suffered a severe sudden cardiac arrest or similar trauma). For example, using the −5 to +5 scoring technique described above, a supervisor may be presented with scores for a dozen recent incidents for a rescuer, and may notice that the scores are generally below 0. The supervisor may then determine to provide the rescuer with training in being more aggressive (i.e., providing harder chest compressions, and reacting more quickly to prompts during a CPR interval). In some additional examples, a + or − score for each CPR parameter can be provided instead of or in addition to the composite score.

Figure 4:
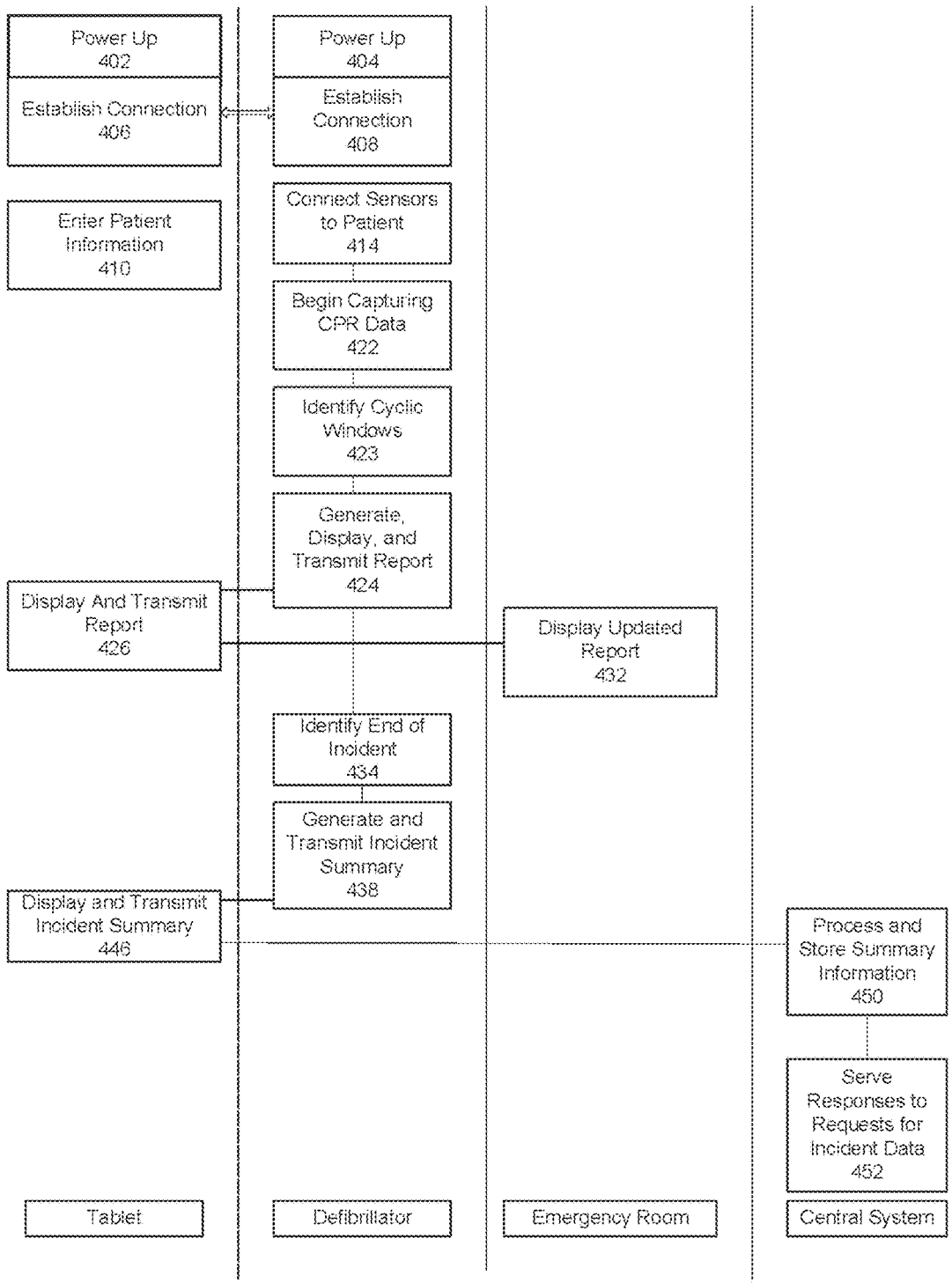
FIG. 4 is a swim lane diagram of a process for sharing CPR performance data between various sub-systems in a larger healthcare system.

FIG. 4 is a swim lane diagram of a process for sharing CPR performance data between various sub-systems in a larger healthcare system. In general, the process discussed here is similar to those discussed above, though actions performed on particular components of a larger system are shown in more detail to indicate examples of a manner in which such actions may be performed in one implementation.

The process begins at an accident scene, were a rescuer has deployed equipment from a rescue vehicle, such as a defibrillator and an associated computing device such as a tablet computer, that may communicate with the defibrillator through a wireless data connection. At boxes 402, 404, the two devices are powered up by the rescuer, and when they have performed initial activities to become active, they may automatically establish a data connection, such as by performing BLUETOOTH pairing between the devices (boxes 406, 408). The rescuer may then enter patient information, at box 410, into the tablet computer, such as basic information regarding the condition of the patient, blood pressure and pulse for the patient, and gender of the patient. Information such as blood pressure and pulse may be recorded automatically by the tablet, such as by way of wired or wireless connection with tools for taking the victim's blood pressure and pulse.

At box 414, the rescuer connects sensors to the patient. For example, the rescuer may open a shirt of a patient and place defibrillation pads on the patient. The defibrillation pads may also include ECG electrodes for sensing cardiac activity of the patient. At this point, the defibrillator may begin performing according to standard protocols for delivering care to a patient, such as by analyzing cardiac activity of the patient. Such action may also lead to the rescuer performing chest compressions and other CPR activities on the patient. Thus, at box 422, the defibrillator may begin capturing CPR data, such as depth and rate of compressions data and other data discussed above. Also, the defibrillator may identify the beginning point for each interval or cycle in the performance of CPR, so as to associate the data with a particular cycle. At box 424, the defibrillator generates, displays, and transmits a report regarding data that is being captured from the performance of CPR. Such a report may take a variety of forms. For example, the report may simply indicate initial or primary parameters that are being captured in real time, and the reporting for those parameters may be continuously updated such as every second or portion of a second. Later, the report may include such real-time data, but may also include summarized, secondary data for one or more CPR intervals or for an entire time period of an incident.

At various points in time, the defibrillator may also transfer data for generating similar reports to the tablet computer, and the tablet computer may display information related to the provision of CPR to the patient, and may also to further transmit the data to a computing device in an area of an emergency room where the victim is to be taken (box 426). The information may then be displayed as a report in the emergency room. The report for the emergency room may take the same form or different forms than that shown on the defibrillator or the tablet computer. For example, if one is to assume that the viewer in the emergency room can give less attention to the report than can the rescuer, the emergency room report may provide less information and be updated less frequently than is the report on the defibrillator or the tablet computer. Particular values that are shown in each report, the frequency with which they are updated, the manner in which they are displayed, and the order in which they are displayed may vary depending on the particular application and the needs of the particular users.

At box 434, the defibrillator identifies that the incident has ended. For example, if no ECG signals are received for a predetermined period of time, the defibrillator may assume that it has been disconnected from the victim and that it will not be used on the victim again. Other mechanisms for determining that an incident has ended are discussed above. When such a determination is made, the defibrillator may transfer its remaining data to the tablet computer and may also generate a summary of the incident and transmit that summary to the tablet computer (box 438). At box 446, the tablet computer displays the summary and also transmits information for the summary to a central server system. Such transmission may be directed toward providing a semi-permanent or permanent record regarding the care that was provided to the victim.

Thus, at box 450, the central server system processes the information received from the tablet computer and stores information about the incident. In certain embodiments, all or substantially all of the information captured by the defibrillator may be stored. Where space limitations or other considerations prevail, summary information may be stored. For example, average values for various parameters may be stored for each cardiac or CPR interval, rather than storing raw values for much smaller but more numerous time segments within each interval.

At some later date, the rescuer or another individual may be interested in analyzing the data that was saved for the particular incident or a group of incidents. Therefore, at box 452, when such a request is received by the central server system, the system may serve responses to the request for data about the incident or other incidents. At the time of serving the data for the incident, the central server system may generate one or more additional reports for presenting the information about the incident or incidents. For example, graphs for each incident at which a particular rescuer acted may be displayed side-by-side, and trend lines or other trend features may be displayed, so that the progression in the skills of a rescuer may be judged, and a reviewer or the rescuer may determine whether the rescuer needs to adjust his or her approach to providing care in a rescue situation.

As discussed above, when a determination is made that a rescue incident has ended, the defibrillator transfers data to a computer and the computer generates a summary of the incident. This summary can include a CPR performance metric such as single score or grade for the entire rescue session (e.g., an alpha-numeric score). This CPR performance metric can provide useful, high-level information to the rescuer about their performance by providing a single alpha-numeric score that gives the rescuer an indication of how well they performed the CPR relative to pre-established guidelines. The CPR performance metric, e.g., the score or grade, can be presented within a limited time (e.g., within less than 5 min) after completion of the rescue attempt (e.g., within a limited time after the cessation of CPR chest compressions). In some applications, the CPR performance metric can be presented to the user within 1 minute or less after completion of the rescue attempt. It is believed that presenting the information quickly will help the rescuer to better correlate the score with their performance and infer ways to improve their future performance.

The CPR performance metric can be an indicator that summarizes CPR performance parameters (e.g., a percentage, a letter grade, a score on a predefined scale such as 1-10). The CPR performance metric is based on CPR parameters such as rate of CPR compressions, depth of CPR compressions, compression fraction (e.g., a measure of interruptions to CPR compressions), ventilation rate, pre-shock pause, and/or post-shock pause. These factors are weighted such that the CPR performance metric can be correlated with of survival rate. As such, a better score of the CPR performance metric can indicate that CPR performance has been optimized for maximum chances of survival for the victim.

The algorithms used to generate the CPR performance metric can be generated using a linear regression technique and or using a neural network analysis technique. For example, the different measured factors or parameters (e.g., rate, depth, and fraction) can be input into a linear regression or other analytical model such as a neural network which can adapt the model to derive a predictor of survival. The weightings that are assigned to each of the parameters can then be optimized based on maximizing the survival rate. After generating the model and training the model using past performance data and clinical outcomes, the model can then be used to provide real-time or substantially immediate feedback to a rescuer based on their performance for a particular rescue attempt. This will include inputting the various factors such as rate, compression depth, fraction, and any other factors used by the model, weighting the factors based on the model, and calculating the performance metric. The performance metric can be displayed to the rescuer in a variety of formats. In some additional examples, in addition to factors such as rate, compression depth, fraction, the performance metric could additionally be based on patient size (e.g. weight, chest diameter, chest circumference), gender, and/or age.

Figure 5:
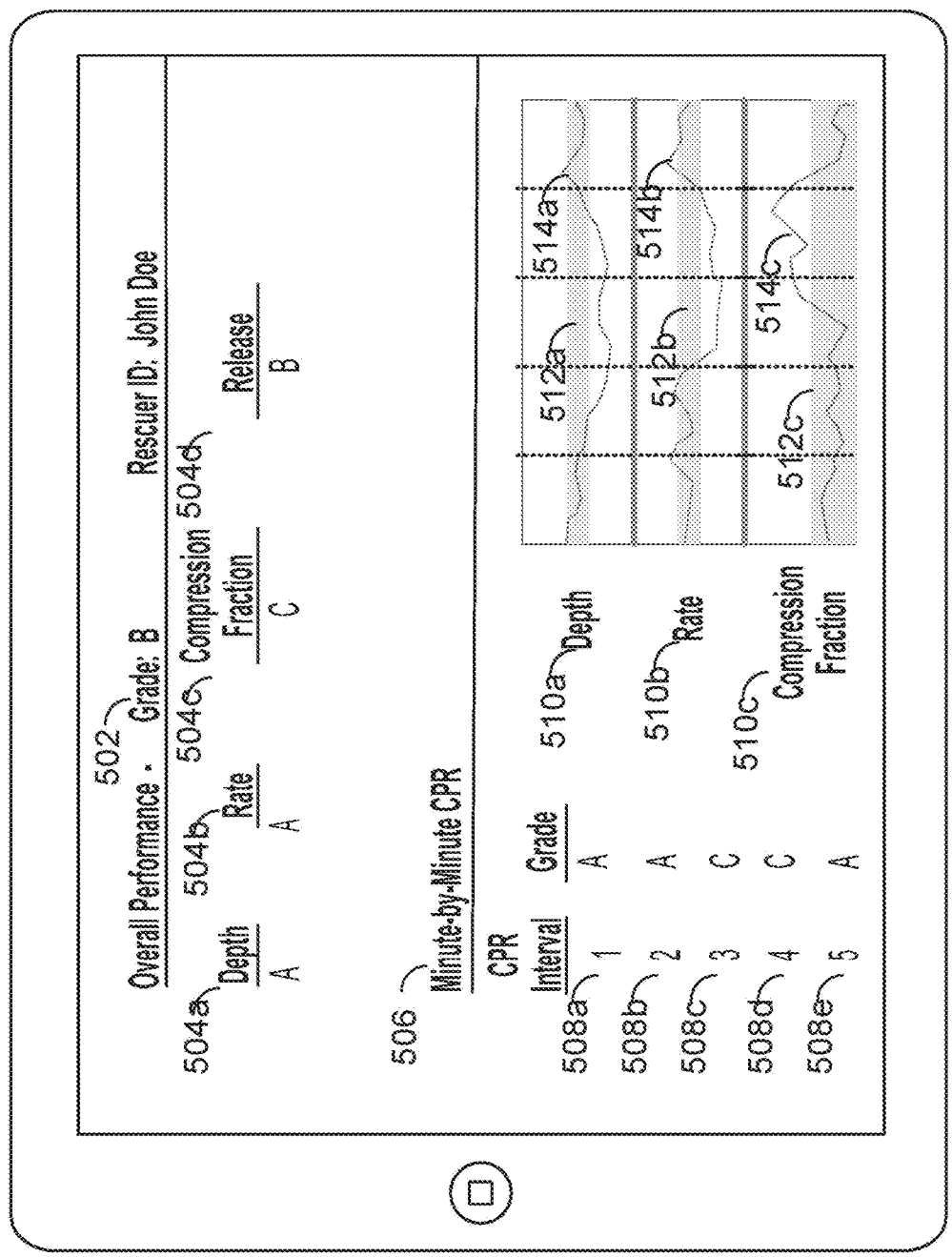
FIG. 5 shows a screen shot of a tablet device showing a summary of rescuer performance.

FIG. 5 is a screenshot of the tablet device showing a summary of rescuer performance in the CPR setting after the completion of the rescue attempt. The presentation of information in this example is split into two portions—a top portion dedicated to overall performance and a bottom portion dedicated to displaying performance information for smaller time periods, such as minute-by-minute. The information presented to the rescuer immediately subsequent to completion of the rescue attempt includes the overall performance metric, which in this case is displayed as performance grade 502.

Referring now to particular portions of the display, a rescuer is shown their overall performance in the form of a grade 502. The overall grade 502 provides an easily understandable measure of the overall performance. In addition to providing the grade 502 for overall performance of CPR, information about multiple key factors in determining overall performance can additionally be displayed. In the example shown in FIG. 5, this information includes a grade for the depth of CPR compressions 504*a*, a grade for the overall rate of CPR compressions 504*b*, a grade for compression fraction 504*c*, and a grade for compression release 504*d*. These scores for the individual factors can help the rescuer to understand why they have received the overall grade 502 and help the rescuer to know how to improve their overall performance. The grade can be similar to a grade scale used by a learning institution and include F, D, C, B, and A grades. The display can also include a rescuer ID to allow each rescuer to know how their performance related to guideline performance. For example, in a multi-rescue performance overall performance can be displayed separately for each rescuer.

Referring now to the second portion of the display, in addition to providing overall performance metrics which relate to the performance across the entire rescue attempt, additionally, performance information is displayed for smaller time intervals 508*a*, 508*b*, 508*c*, 508*d*, and 508*e*, such as minute-by-minute. In this example, for each of multiple CPR intervals, the display includes a grade for that interval. The grade for that interval is generated based on performance data collected during the associated time period. Displaying grades for more finely subdivided time intervals can help the rescuer to understand whether their overall performance improved or degraded during the rescue attempt. For example, in the exemplary display shown in FIG. 5, the rescuer performed well in the first two time intervals and the final time interval but the rescuer's performance degraded during time intervals, three and four. As such, upon review, the rescuer could think about differences in how they performed the rescue during the time intervals for which they received lower grades and use that information to improve their CPR technique.

Additionally, the second portion of the display includes graphical information about key performance factors. For example, the depth of CPR compressions, rate of CPR compressions, and compression fraction metrics are individually displayed graphically by portions 510*a*, 510*b*, and 510*c*. In the graphical display, both the actual measured parameter and an acceptable range of parameters can be displayed to the rescuer. For example, in the graph of depth 510*a*, an acceptable range of depth is indicated by shaded portion 512*a* and the actual depth measured for the compressions performed during the rescue attempt is displayed as line 514*a*. Displaying both the acceptable range and measured data for the parameter allows the rescuer to see how their performance varied during the rescue attempt and to understand how their performance deviated from desired performance (e.g., performance as provided in CPR guidelines).

Figure 6:
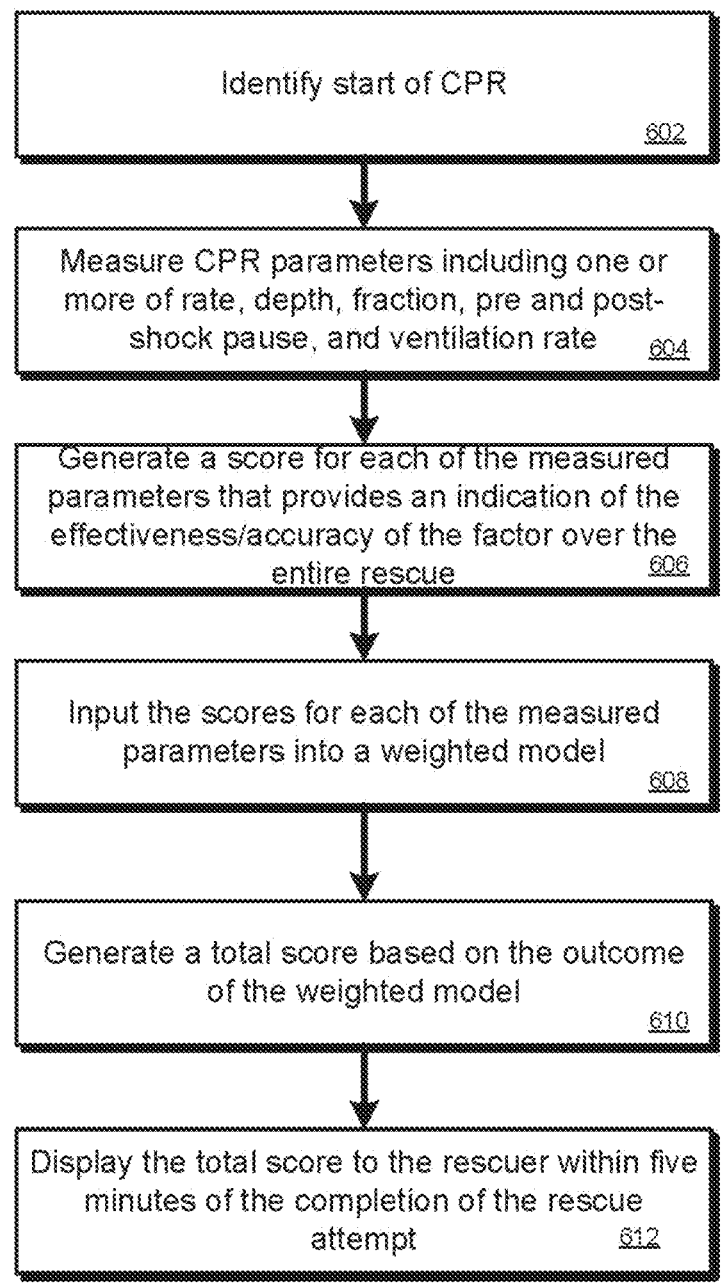
FIG. 6 is a flow chart of a process for generating a CPR performance metric.

FIG. 6 is a flowchart of a process for generating the CPR performance metric. In general, the process involves receiving information about CPR parameters such as rate, depth, fraction, pause, and/or ventilation, and inputting the information into a weighted model, to generate and display a CPR performance metric within a limited time after completion of the rescue attempt (e.g., within one minute of completion).

The process begins at box 602, where a defibrillator with built-in capabilities for monitoring motion of chest compressions and ECG signals, among other parameters monitors inputs to generate information about the patient and CPR performance. This information is used to identify that CPR has begun.

At box 604, sensors are used to collect information and data about the CPR activities. This information can include information about the rate of CPR chest compressions, depth of CPR chest compressions, fraction in compressions, pauses prior to or subsequent to defibrillation, and ventilation rate. The particular activities performed during CPR may generate data from the sensors and the step of measuring these parameters can also include converting the data to a more usable form. For example, the voltage received from accelerometer can be used to compute a depth of compression.

At box 606, a computer or processing device calculates the score for each of the measured parameters. These per-parameter scorers provide an indication of the effectiveness or accuracy of the factor over the entire rescue performance. For example, a desired depth range for CPR chest compressions can be 2.0 inches. Based on a comparison of the actual measured depths to the desired depth, the system can calculate a chest compression depth score that is indicative of how closely the performed chest compression depth match the desired depth. Similarly, based on other desired ranges, the other performance factors can provide a measure of how well the rescuer has stayed within the desired performance ranges. In one particular example, the per-parameter score can be a percentage of the CPR that was within guidelines. For example, the percentage of compressions having a measured depth that is within the desired compression depth range outlined by the CPR guidelines. In some examples, the parameter is summarized based on whether the patient has return of spontaneous circulation (ROSC). If a patient obtains ROSC 10 seconds into an interval, the chest compressions fraction will be very low. Thus, excluding this data can provide more useful information for the rescuer about their rescue technique.

At box 608, the individually generated per-parameter scorers are entered into a weighted model. The weighted model can be generated according to a variety of mathematical processes, such as by using a linear regression or other analytical model such as a neural network, which is been previously trained based on CPR performance data and patient outcome associated with the performance data.

At box 610, the system generates a CPR performance metric score based on the outcome of the weighted model calculation. The CPR performance metric score provides a single value or parameter indicative of the overall performance throughout the entire rescue. For example, the CPR performance metric (CPM) score can be calculated according to the following:

$$CPM=f\ (w_{rate}*X_{rate}, w_{Depth}*X_{depth}, w_{fraction}*X_{fraction})$$

where $w_{rate}$, $w_{depth}$, and $w_{fraction}$ are weighting factors for rate, depth and fraction and $X_{rate}$, $X_{depth}$, and $X_{fraction}$ are calculated metrics for the overall performance of CPR rate, depth, and fraction relative to a guideline or desired performance. At box 612, the total score is displayed to the rescuer within a limited time after the completion of the rescue attempt. For example, the score can be displayed within 5 minutes of completion of the rescue attempt. In another example, the score can be displayed within one minute of completion of the rescue attempt.

In some examples, only data collected prior to arrival of the victim at the hospital (e.g., prehospital data) is used to generate the performance metrics. Thus, the system identifies when the victim has arrived at the hospital and excludes any subsequent data from the performance metric calculations. In some additional examples, the system could calculate the performance metrics upon receipt or determination of an end of case indictor which could be time of pad removal, time that a soft key is pressed to indicate case end, time of arrival at ED as determined from GPS or dispatch.

Figure 7:
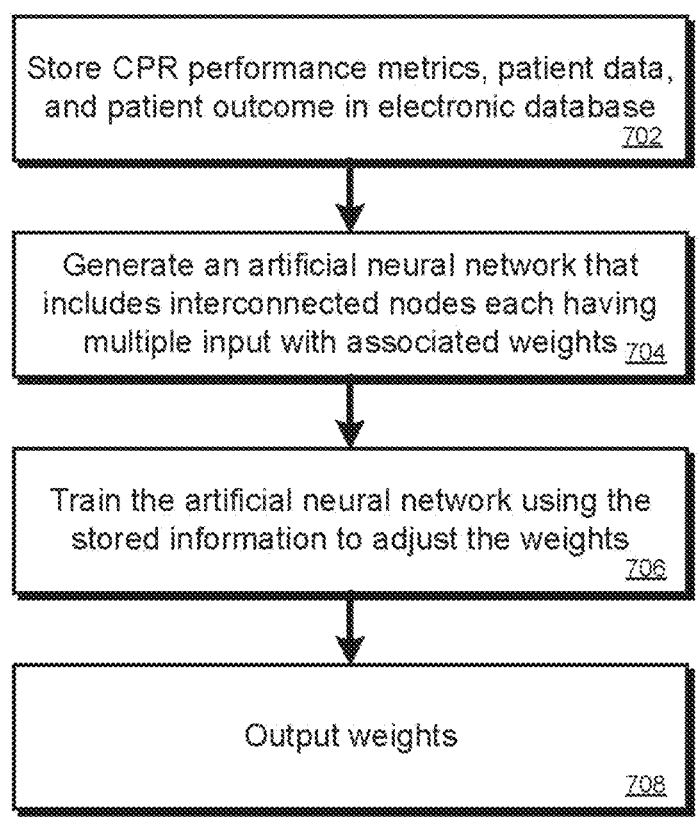
FIG. 7 is a flow chart of a process for training a model.

FIG. 7 is a flowchart illustrating a method for producing an artificial neural network capable of generating the CPR performance metric. In general the neural network receives sets of data from past rescue attempts and trains a neural network model based on the data. This generates weightings for various factors that are used to calculate the CPR performance metric.

At box 702, CPR performance information and patient outcome information are stored in an electronic database. More particularly, the data can include a plurality of sets of data with each set having multiple parameters related to CPR performance such as rate, depth, and fraction. Additionally, each of the sets of data has a parameter relating to patient outcome such as whether the patient survived.

At box 704, a computer-generated artificial neural network that includes interconnected nodes is generated. Each node has multiple inputs and associated weights. The nodes include a plurality of artificial neurons, each artificial neuron having at least one input and associated weight. For example, the neural network maybe a mathematical model or computational model simulating the structure and/or functional aspects of the biological neural network.

At box 706, the system trains the artificial neural network using the stored information about the CPR performance and patient outcome. This training adjusts the weights of at least one input of each artificial neuron of the plurality of artificial neurons responsive to the different parameters in the different sets of data. This results in the artificial neural network being trained to produce a prediction of the patient outcome based on the CPR performance data. For example, as noted above, artificial neural networks are based on pattern recognition tasks and are used to provide artificial intelligence-based approach to solve classification problems. Thus, a model is formed during the training process using previously known input/output pairs. The trained model can then be tested with new data to verify the model and subsequently used to provide a desired output. Various known artificial neural network topologies can be used to generate the CPR performance metric. Exemplary neural network topologies include single layer and multilayer feed-forward networks which are based on weights of hidden layers that are adjusted during training to minimize an error function. Training of the artificial neural network can be based on back propagation learning, such as use of the Levenberg-Marquardt algorithm. At box 708, the weights for the various parameters are stored. These weights can later be used to calculate the performance metric for a new set of CPR performance data.

In some examples, the model can also be based on information about the patient such as weight, age or gender.

Figure 8:
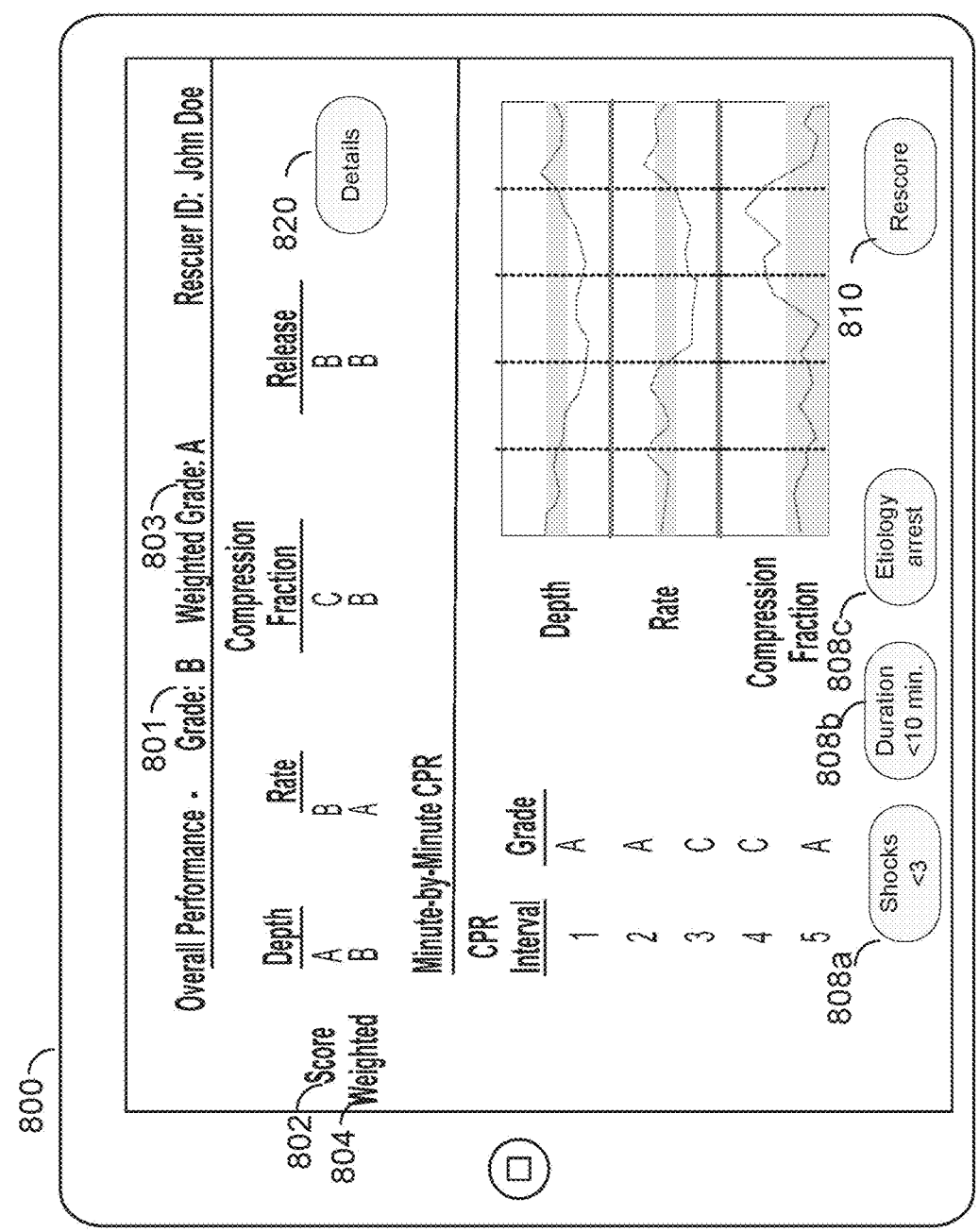
FIG. 8 shows a screen shot of a tablet device showing a summary of rescuer performance.

FIG. 8 is a screenshot of a tablet device showing a summary of rescuer performance in the CPR setting after the completion of the rescue attempt. Similar to the screenshot shown in FIG. 5, the presentation of information in this example is split into two portions—a top portion dedicated to overall performance and a bottom portion dedicated to displaying performance information for smaller time periods, such as minute-by-minute. The information presented to the rescuer immediately subsequent to completion of the rescue attempt includes an overall performance metric 801 and a weighted performance metric 803.

Weighted metrics can be provided based on particular factors relevant to the rescue attempt. For example, if a victim receives a large number of shocks, then the unweighted score for compression fraction may provide an unnecessarily low indication of the rescuer's performance due to breaks or pauses in CPR during administration of the shock. Similarly, a rescuer's performance may be judged differently if the rescue attempt is short versus a lengthy rescue attempt. In order to provide relevant feedback to the rescuer, such factors can be taken into account when calculating a weighted performance metric. In one particular example information about the number of shocks, etiology of the arrest, and/or duration of the rescue attempt (e.g., duration of CPR administration) can be factored into the weighted score 803 that is provided to the rescuer.

In one particular example, the CPR performance metric (CPM) score can be calculated according to the following:

$$CPM=f\ (w_{rate}*X_{rate}, w_{Depth}*X_{depth}, w_{fraction}*X_{fraction})$$

and the weighted performance metric can be calculated according to the following:

$$CPM=f\ (w_{rescue,rate}*w_{rate}*X_{rate},\\ w_{rescue,depth}*w_{Depth}*X_{depth},\\ w_{rescue,fraction}*w_{fraction}*\\ X_{fraction})$$

where $w_{rate}$, $w_{depth}$, and $w_{fraction}$ are weighting factors for rate, depth and fraction, $w_{rescue,rate}$, $w_{rescue,depth}$, and $w_{rescue,fraction}$ are weighting factors for rate, depth and fraction based on particular features of the specific rescue attempt and $X_{rate}$, $X_{depth}$, and $X_{fraction}$ are calculated metrics for the overall performance of CPR rate, depth, and fraction relative to a guideline or desired performance. In another example, in order to calculate the weighted metrics, sub-portions of the performance data can be given a greater weighting and/or portions of the performance data can be excluded from consideration in the weighted metric calculation. For example, a period of time surrounding an event (e.g., defibrillation, intubation, etc) can be weighted differently than other periods of time by having lesser or greater influence on the score than other periods of time. In one particular example, a compression pause around the time of a shock may be weighted to have a greater influence on the score since such a pause is likely to have a greater impact on the patient.

In one particular example, a rescuer is shown their overall performance in the form of two grades 801 and 803. An overall grade 801 provides an easily understandable measure of the overall performance and a weighted grade 803 provides a measure of overall performance that is weighted based on characteristics particular to the rescue attempt (e.g., characteristics that would differ from one rescue attempt to another). The weighted grade 803 can be higher or lower than the overall grade 801 due to factors influencing the performance of the rescuer and/or factors influencing the advisable treatment. In addition to providing the grade 801 and the weighted grade 803 for overall performance of CPR, information about multiple key factors in determining overall performance can additionally be displayed. This information includes both weighted and unweighted grades/scores 804, 802 for the depth of CPR compressions, overall rate of CPR compressions, compression fraction, and compression release. These scores for the individual factors can help the rescuer to understand why they have received the overall grade and help the rescuer to know how to improve their overall performance.

In some examples, the weighted grade can be generated automatically based on input received from the defibrillation device about the treatment such as the number of shocks and duration of treatment. In other examples, a user can input or modify key factors that are used to generate the weighted score by selecting the appropriate buttons. For example, a user can change the number of shocks that were administered by selecting button 808a, modify the duration of the rescue attempt by selecting button 808b, and/or modify the etiology of the arrest by selecting button 808c. Other user modifiable factors can additionally or alternatively be provided. For example, a user could change the weight of a patient and/or the chest size of a patient prior to generating the weighted grade. Modifying parameters related to the actual treatment can change the acceptable range of values for depth, rate, fraction, and/or release. For example, the protocol used to score a rescue attempt for an arrest of respiratory etiology versus cardiac etiology would likely differ. After modifying one or more of the parameters, the user can select the rescore button 810 you have a new or updated weighted score generated based on the updated parameters.

Figure 9A:
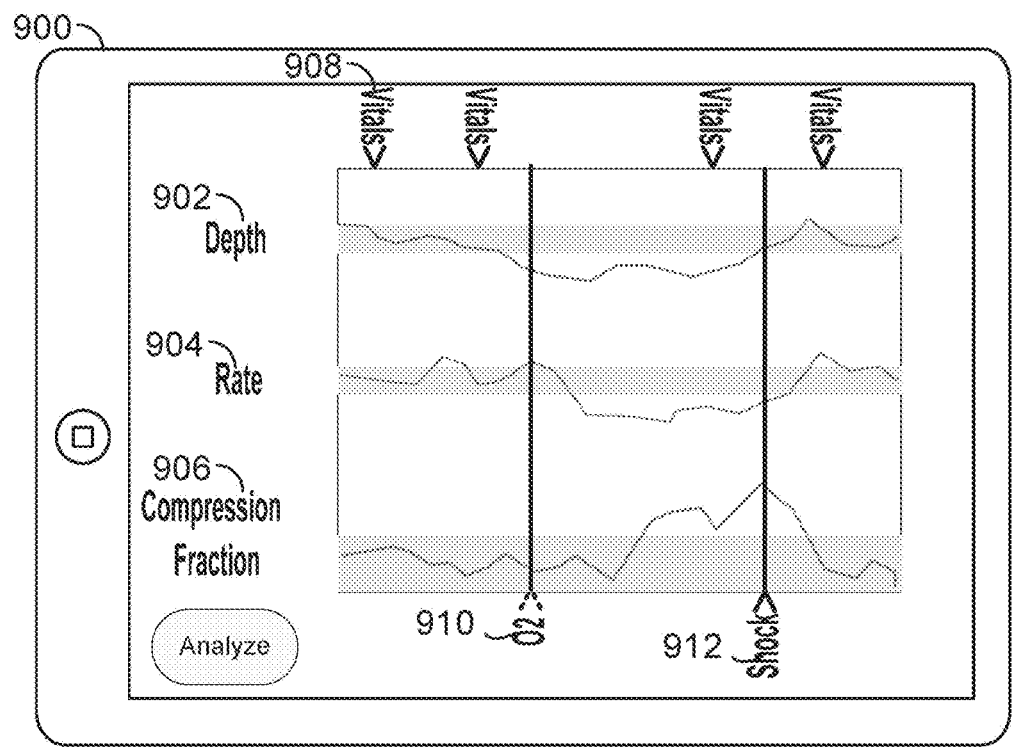
FIGS. 9A and 9B shows a screen shot of a tablet device showing performance data.
Figure 9B:
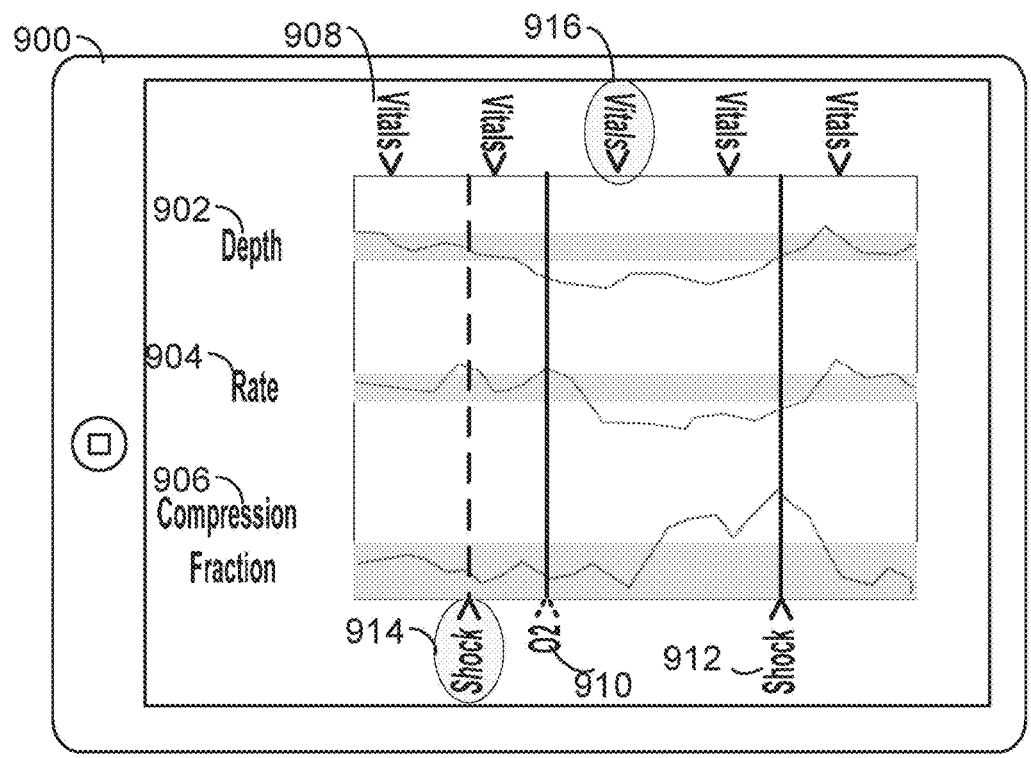

FIGS. 9A and 9B show exemplary user interfaces for a time-based feedback that includes visual indicia associated with interventions and events during the rescue attempt overlaid onto one or more of the measured parameters. The user can access this information by selection of button 806 in user interface 800 of FIG. 8.

As shown in FIG. 9A, the display includes graphical information about key performance factors. For example, the depth of CPR compressions, rate of CPR compressions, and compression fraction metrics are individually displayed graphically by portions 902, 904, and 906. In the graphical display, both the actual measured parameter and an acceptable range of parameters can be displayed to the rescuer. For example, an acceptable range of depth is indicated by shaded portion and the measured value is displayed as a line. Displaying both the acceptable range and measured data for the parameter allows the rescuer to see how their performance varied during the rescue attempt and understand how their performance deviated from desired performance (e.g., performance as provided in CPR guidelines). In some examples, the acceptable range could be automatically adjusted based upon patient information such patient age or patient size.

In addition to displaying the time-based performance factors, indicators can be used to display information about the timing defibrillation shock administration, vital assessment, oxygen administration, and/or other events during the rescue attempt. For example, a visual indicator 908 can be displayed on the time-based graph to show when vitals were measured and recorded by the rescuer. In another example, an indicator 910 can be used to display when the administration of oxygen began and/or an indicator 912 can be used to display when a defibrillation shock was administered. This information can provide the trend of the overall rescue attempt with an indication of when interventions occurred.

FIG. 9B shows the time-based feedback that includes marked interventions and events during a rescue attempt with additional information about additional interventions or modifications in treatment that could be deemed desirable based on a protocol. This information can be displayed to the rescuer to provide instruction on how the rescue attempt might have been improved. For example, in a typical arrest vitals should be taken approximately every 5 min. In the example of FIG. 9B, an additional indication 916 is added to the display to show a time point at which it would have been beneficial for the rescuer to have retaken the vitals. Additionally, analysis can be done to determine if and when additional defibrillation shocks may have been beneficial (e.g., a shock should have been provided but was missed) and/or when a shock was administered during a non-shockable rhythm or time (e.g., when a shock was provided but it would have been more appropriate not to shock the patient). Such information can be displayed on the user interface (e.g. see line 914) to allow the rescuer to better understand how their rescue performance might be improved.

While in at least some of the examples described above, information about CPR performance was relayed to the rescuer on a user interface, additional information and/or different information can be relayed to the rescuer during traumatic brain injury treatment. For example, a different set of parameters can be displayed when a traumatic brain injury is suspected or diagnosed based on the patient physiological data, charting data, and/or following a clinical analysis process. For example, the monitor may be configured to automatically obtain and display vital signs (e.g. blood pressure, SpO2, EtCO2, heart rate, and respiratory rate). As such, the information displayed to a rescuer during a rescue attempt for a traumatic brain injury victim differs from the information displayed to a rescuer during a CPR resuscitation attempt.

Figure 10:
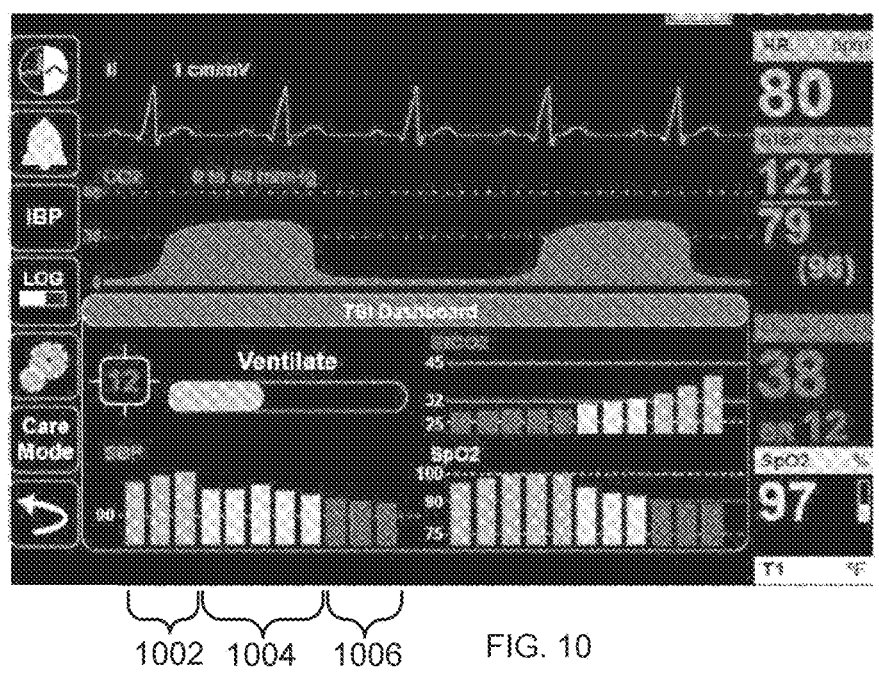
FIG. 10 shows a screen shot of a tablet device showing rescuer performance data during treatment of a traumatic brain injury.

FIG. 10 illustrates a user interface, for example a user interface for a patient monitor/defibrillator or other device. The user interface of FIG. 10 includes display portions which indicate trending information for various values. For example, the interface illustrates trending data for systolic blood pressure, end tidal carbon dioxide (EtC02), and blood oxygen saturation (Sp02). Trending data may be displayed as a running record of previous readings. The oldest readings may appear on the left, and the newest readings may appear on the right, and the newest reading may be inserted on the right side while displacing the oldest reading on the left side. Alternatively, the oldest readings may appear on the right, and the newest readings may appear on the left, and the newest reading may be inserted on the left side while displacing the oldest reading on the right side. Other options for visually indicating the trend data for a given signal may be employed.

Additional information about how the trending values compare with acceptable values or ranges can be displayed on the patient monitor/defibrillator to help a clinician assess patient history and condition. According to some embodiments, the scaling of the trending readouts, and/or the frequency of the values displayed for the trending values, and/or a color in which the trending values are displayed, is customized according to the particular patient and/or the patient's condition.

In the example of FIG. 10, the three bars on the left 1002 may be displayed as green to indicate that the patient's blood pressure at the times corresponding to those particular blood pressure measurements was within acceptable limits for the patient's age. The middle five bars 1004 may be yellow to indicate that the patient's blood pressure at the times corresponding to those particular blood pressure measurements was below acceptable limits, but not yet at a critical level. The right three bars 1006 may be red to indicate that the patient's blood pressure at the times corresponding to those particular blood pressure measurements was far below acceptable ranges, and was therefore at a critical level. In embodiments in which the newest trending values appear on the right side, the trend graph for patient systolic blood pressure indicates that the patient's blood pressure is worsening over time by becoming lower. Of course, other colors may be used, and additional colors and/or ranges may be employed. These ranges may be automatically adjusted based on various factors, for example the patient's age, or other conditions. For example, all of the bars 1002, 1004, and 1006 can be displayed as green for a normal adult patient, while the same absolute readings may be colored for a younger or adolescent patient. The coloring, target ranges, or other visual indication of the trending data may also be adjusted during the patient monitoring event, based on data observed by the patient monitoring device. Further information and examples of traumatic brain injury treatment and display can be found, for example, in U.S. Patent Application No. 61/818,334 titled "EMS Decision Support Interface, Event History, and Related Tools", the contents of which is hereby incorporated by reference in its entirety.

According to some embodiments of the present invention, if a patient has cerebral herniation or impending cerebral herniation, the ETC02 and/or ventilation rate targets may be changed in order to hyperventilate such patients so as to reduce intracranial pressure. These ranges or targets may be adjusted automatically if, in the course of a decision support process, the system detects, either automatically, or via manual or clinical or other inputs, that the patient has or is about to experience cerebral herniation.

Figure 11A:
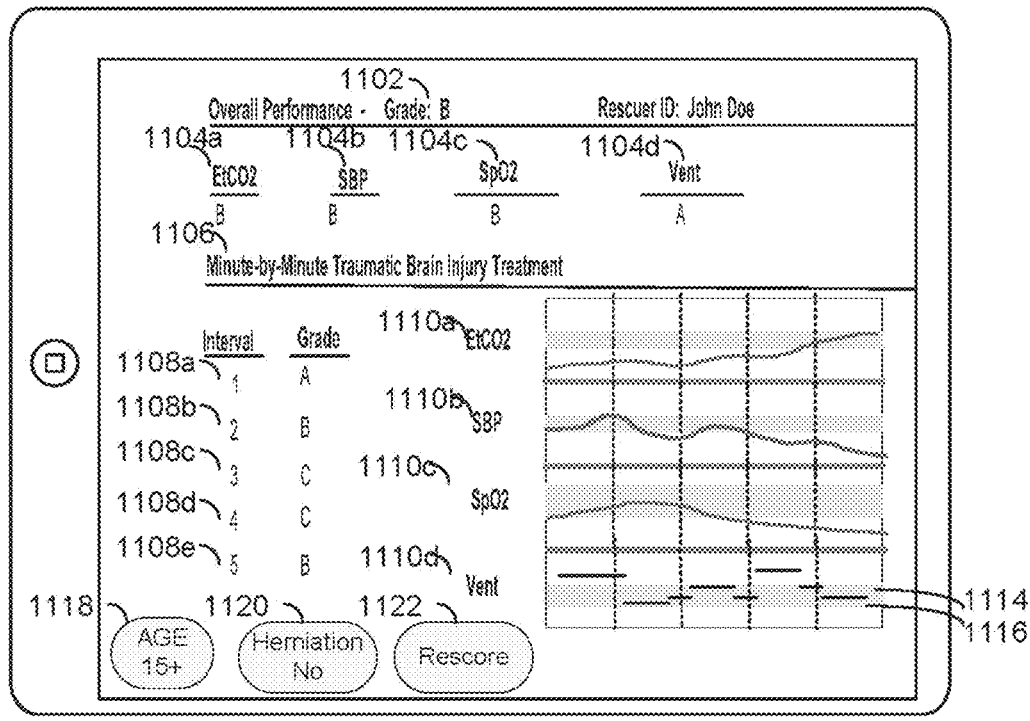
FIGS. 11A and 11B show screen shots of a tablet device showing a summary of rescuer performance during treatment of a traumatic brain injury.

FIG. 11A is a screenshot of the tablet device showing a summary of rescuer performance in the traumatic brain injury setting after the completion of the rescue attempt. The presentation of information in this example is split into two portions—a top portion dedicated to overall performance and a bottom portion dedicated to displaying performance information for smaller time periods, such as minute-by-minute. The information presented to the rescuer immediately subsequent to completion of the rescue attempt (e.g., within 1 minute or within 5 minutes) includes the overall performance metric, which in this case is displayed as performance grade 1102.

Referring now to particular portions of the display, a rescuer is shown their overall performance in the form of a grade 1102. The overall grade 1102 provides an easily understandable measure of the overall performance. In addition to providing the grade 1102 for overall performance of treatment of the traumatic brain injury, information about multiple key factors in determining overall performance can additionally be displayed. In the example shown in FIG. 11A, this information includes a grade for the EtCO2 1104a, a grade for the Systolic blood pressure 1104b, a grade for SpO2 1104c, and a grade for ventilation rate 1104d. These scores for the individual factors can help the rescuer to understand why they have received the overall grade 1102 and help the rescuer to know how to improve their overall performance. The grade can be similar to a grade scale used by a learning institution and include F, D, C, B, and A grades or can be a numeric score. In some examples, an additional label of unknown or not applicable label could be provided rather instead of a grade if the parameter was not captured. For example, if the rescuer did not have the capability to measure EtCO2 rather than provide a grade of 'F' the system could provide a notification that the EtCO2 was not measured or factored into the score.

Referring now to the second portion of the display, in addition to providing overall performance metrics which relate to the performance across the entire rescue attempt, additionally, performance information is displayed for smaller time intervals 1108a, 1108b, 1108c, 1108d, and 1108e, such as minute-by-minute or 5 minute intervals. In this example, for each of multiple time intervals, the display includes a grade for that interval. The grade for that interval is generated based on performance data collected during the associated time period. Displaying grades for more finely subdivided time intervals can help the rescuer to understand whether their overall performance improved or degraded during the rescue attempt.

The second portion of the display also includes graphical information about key performance factors. For example, the ETCO2, SBP, SpO2, and ventilation rate are individually displayed graphically by portions 1110a, 1110b, 1110c, and 1110d. In the graphical display, both the actual measured parameter and an acceptable range of parameters can be displayed to the rescuer. For example, in the graph of ventilation 1110d, an acceptable rate range is indicated by shaded portion 1114 and the actual ventilation rate measured is displayed as line 1116. Displaying both the acceptable range and measured data for the parameter allows the rescuer to see how their performance varied during the rescue attempt and to understand how their performance deviated from desired performance (e.g., performance as provided in guidelines).

As noted above, acceptable ranges for various measured parameters can be adjusted based on various factors, for example the patient's age, whether the patient is experiencing herniation, or other conditions. Since these factors will influence the scoring of the rescue attempt after completion of the rescue attempt, the system can provide a mechanism to re-score the rescue attempt. For example, a user can input factors about the rescue, such as the patient age and whether herniation exists using buttons 1118 and 1120. After such information has been updated, the user can select button 1112, to cause the system to rescore the rescue attempt based on the updated protocol information.

Figure 11B:
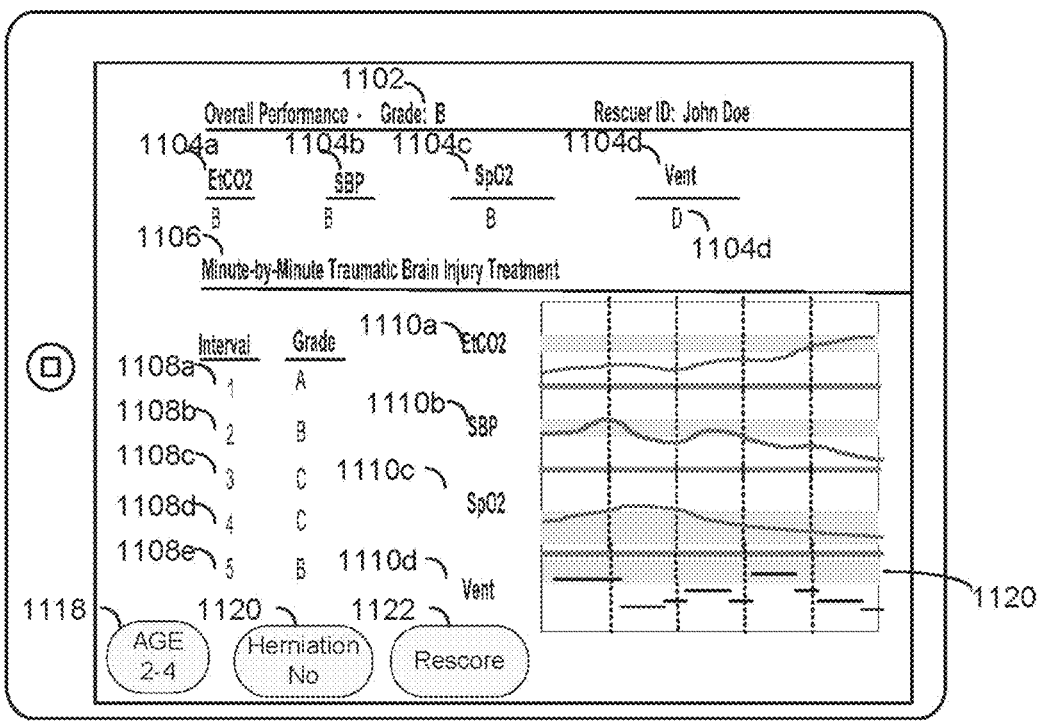

For example, in FIG. 11B, the age of the traumatic brain injury victim has been modified from being over 15 (FIG. 11A) to being a child of age 2 years. The protocol for treating a traumatic brain injury in a 2 to 4-year-old victim relies on a much higher ventilation rate than the protocol for treating an adult. As such, the acceptable range of ventilation rate is modified as the age is updated (as indicated by the difference in shaded region 1114 and shaded region 1120). As the acceptable range of values is modified, the measured values falling within the acceptable range and outside of the acceptable range are also modified. For example, in FIG. 11B, many of the measured ventilation rate values which were previously within an acceptable range fall outside of the acceptable range after the protocol is modified based on the updated patient age. Thus, re-scoring a rescue attempt can provide useful feedback to the user because the appropriate protocols are then used to provide feedback on performance.

Figure 12:
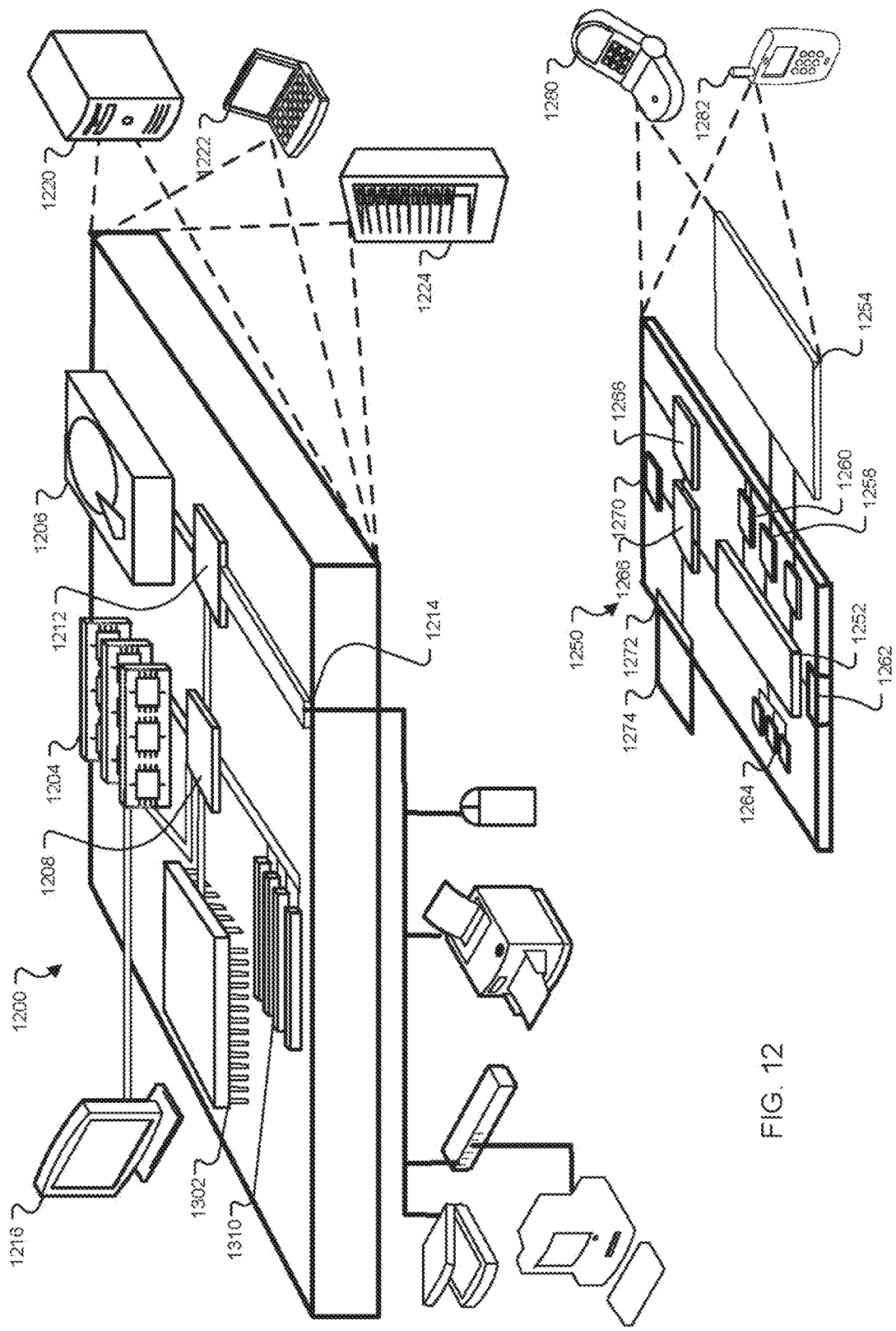
FIG. 12 shows an example of a generic computer device and a generic mobile computer device, which may be used with the techniques described here.

A similar re-scoring process could be applied to the CPR scoring. In such a process, upon receiving updated information from the user, the system would update the protocols used to score the CPR administration. Using the updated protocols, the system generates updated score(s) for the rescue attempt FIG. 12 shows an example of a generic computer device 1200 and a generic mobile computer device 1250, which may be used with the techniques described here.

Computing device 1200 is intended to represent various forms of digital computers, such as laptops, desktops, workstations, personal digital assistants, servers, blade servers, mainframes, and other appropriate computers. Computing device 1250 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 1200 includes a processor 1202, memory 1204, a storage device 506, a high-speed interface 1208 connecting to memory 1204 and high-speed expansion ports 1210, and a low speed interface 1212 connecting to low speed bus 1214 and storage device 1206. Each of the components 1202, 1204, 1206, 1208, 1210, and 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as display 1216 coupled to high speed interface 1208. In other implementations, multiple processors and/or multiple buses may be used, as appropriate, along with multiple memories and types of memory. Also, multiple computing devices 1200 may be connected, with each device providing portions of the necessary operations (e.g., as a server bank, a group of blade servers, or a multi-processor system).

The memory 1204 stores information within the computing device 1250. In one implementation, the memory 1204 is a volatile memory unit or units. In another implementation, the memory 1204 is a non-volatile memory unit or units. The memory 1204 may also be another form of computer-readable medium, such as a magnetic or optical disk.

The storage device 1206 is capable of providing mass storage for the computing device 1200. In one implementation, the storage device 1206 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1204, the storage device 1206, memory on processor 1202, or a propagated signal.

The high speed controller 1208 manages bandwidth-intensive operations for the computing device 1200, while the low speed controller 1212 manages lower bandwidth-intensive operations. Such allocation of functions is exemplary only. In one implementation, the high-speed controller 1208 is coupled to memory 12504, display 1216 (e.g., through a graphics processor or accelerator), and to high-speed expansion ports 1210, which may accept various expansion cards (not shown). In the implementation, low-speed controller 1212 is coupled to storage device 1206 and low-speed expansion port 1214. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. It may also be implemented as part of a rack server system 1224. In addition, it may be implemented in a personal computer such as a laptop computer 1222. Alternatively, components from computing device 1200 may be combined with other components in a mobile device (not shown), such as device 1250. Each of such devices may contain one or more of computing device 1200, 1250, and an entire system may be made up of multiple computing devices 1200, 1250 communicating with each other.

Computing device 1250 includes a processor 1252, memory 1264, an input/output device such as a display 1254, a communication interface 1266, and a transceiver 1268, among other components. The device 1250 may also be provided with a storage device, such as a micro drive or other device, to provide additional storage. Each of the components 1250, 1252, 12612, 1258, 1266, and 1268, are interconnected using various buses, and several of the components may be mounted on a common motherboard or in other manners as appropriate.

The processor 1252 can execute instructions within the computing device 1250, including instructions stored in the memory 1264. The processor may be implemented as a chipset of chips that include separate and multiple analog and digital processors. The processor may provide, for example, for coordination of the other components of the device 1250, such as control of user interfaces, applications run by device 1250, and wireless communication by device 1250.

Processor 1252 may communicate with a user through control interface 1258 and display interface 1256 coupled to a display 1254. The display 1254 may be, for example, a TFT LCD (Thin-Film-Transistor Liquid Crystal Display) or an OLED (Organic Light Emitting Diode) display, or other appropriate display technology. The display interface 1256 may comprise appropriate circuitry for driving the display 1258 to present graphical and other information to a user. The control interface 1258 may receive commands from a user and convert them for submission to the processor 1252. In addition, an external interface 1262 may be provide in communication with processor 1252, so as to enable near area communication of device 1250 with other devices. External interface 1262 may provide, for example, for wired communication in some implementations, or for wireless communication in other implementations, and multiple interfaces may also be used.

The memory 1264 stores information within the computing device 1250. The memory 1264 can be implemented as one or more of a computer-readable medium or media, a volatile memory unit or units, or a non-volatile memory unit or units. Expansion memory 1274 may also be provided and connected to device 1250 through expansion interface 1272, which may include, for example, a SIMM (Single In Line Memory Module) card interface. Such expansion memory 1274 may provide extra storage space for device 1250, or may also store applications or other information for device 1250. Specifically, expansion memory 1274 may include instructions to carry out or supplement the processes described above, and may include secure information also. Thus, for example, expansion memory 1274 may be provide as a security module for device 1250, and may be programmed with instructions that permit secure use of device 1250. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1264, expansion memory 1274, memory on processor 1252.

Device 1250 may communicate wirelessly through communication interface 1266, which may include digital signal processing circuitry where necessary. Communication interface 1266 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1268. In addition, short-range communication may occur, such as using a Bluetooth, WiFi, or other such transceiver (not shown). In addition, GPS (Global Positioning System) receiver module 1270 may provide additional navigation—and location—related wireless data to device 1250, which may be used as appropriate by applications running on device 1250.

Device 1250 may also communicate audibly using audio codec 1260, which may receive spoken information from a user and convert it to usable digital information. Audio codec 1260 may likewise generate audible sound for a user, such as through a speaker, e.g., in a handset of device 1250. Such sound may include sound from voice telephone calls, may include recorded sound (e.g., voice messages, music files, etc.) and may also include sound generated by applications operating on device 1250.

The computing device 1250 may be implemented in a number of different forms, as shown in the figure. For example, it may be implemented as a cellular telephone 1280. It may also be implemented as part of a smartphone 1282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to ICU monitoring with attending physicians, but other forms of patient monitoring and reporting may also be addressed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A system for providing summary information about treatment of a patient over two or more time intervals of a rescue event when traumatic brain injury (TBI) is suspected or diagnosed, the system comprising:
   at least one airflow sensor positioned in an airflow path in fluid communication with the patient's airway configured to sense data representative of ventilations provided to the patient;
   at least one patient condition sensor configured to sense data representative of one or more patient condition parameters of the patient when TBI is suspected or diagnosed, the patient condition parameters comprising one or more of systolic blood pressure, end tidal carbon dioxide ($EtCO_2$), or blood oxygen saturation ($SpO_2$);
   a visual display for providing the summary information to a user about treatment of the patient during the rescue event; and
   a controller electrically coupled to the at least one airflow sensor, the at least one patient condition sensor, and the visual display configured to:
      receive and process data sensed for the ventilations provided to the patient from the at least one airflow sensor and data representative of the one or more patient condition parameters from the at least one patient condition sensor;
      generate, from analysis of the received and processed data a first TBI performance metric that condenses the data sensed for the ventilations provided to the patient and for the one or more patient condition parameters over a first time interval into a single metric indicative of performance of at least one rescuer providing treatment for the TBI patient over the course of the first time interval;
      cause the visual display to display summary information for the first time interval comprising the first TBI performance metric to a user to provide an indication of performance of the at least one rescuer over the course of the first time interval;
      generate a second TBI performance metric from analysis of the received and processed data over a second time interval that condenses the data sensed for the ventilations provided to the patient and for the one or more patient condition parameters into a single metric indicative of performance of at least one rescuer providing treatment for the TBI patient over the course of the second time interval; and
      cause the visual display to display summary information to the user for the second time interval comprising the second TBI performance metric to provide an indication of performance of the at least one rescuer over the second time interval.

2. The system of claim 1, wherein the first TBI performance metric and/or the second TBI performance metric comprises a score that indicates by one or more of an alpha and a numeric indicator a quality of care for treatment of the patient.

3. The system of claim 1, further comprising a chest compression sensor for measuring one or more chest compression parameters during performance of cardiopulmonary resuscitation (CPR) for the patient, the chest compression parameters comprising one or more of: compression depth, compression rate, and compression fraction, wherein the first TBI performance metric and the second TBI performance metric are based, at least in part, on one or more of the chest compression parameters, the data sensed for the ventilations provided to the patient, and the one or more patient condition parameters.

4. The system of claim 1, wherein the first TBI performance metric and the second TBI performance metric each comprise a weighted performance metric calculated by applying a weighting factor to data sensed for the ventilations provided to the patient and for each of the one or more patient condition parameters.

5. The system of claim 4, wherein the weighting factor for the data sensed for the ventilations provided to the patient from the at least one airflow sensor and for each of the one or more patient condition parameters comprises a weighting factor determined using a neural network or a linear regression technique.

6. The system of claim 1, wherein the controller is further configured to cause the visual display to display trend graphs for one or more of a ventilation rate determined based on the data sensed for the ventilations provided to the patient from the at least one airflow sensor, a ventilation volume determined based on the data sensed for the ventilations provided to the patient from the at least one airflow sensor, or for the one or more patient condition parameters along with the first TBI performance metric and the second TBI performance metric.

7. The system of claim 1, wherein the controller is further configured to cause the visual display to display a graphical indicator for one or more of a ventilation rate determined based on the data sensed for the ventilations provided to the patient from the at least one airflow sensor, a ventilation volume determined based on the data sensed for the ventilations provided to the patient from the at least one airflow sensor, or the one or more patient condition parameters, the graphical indicator being representative of whether the rate, volume, or patient condition parameter is within an acceptable limit over the course of the rescue event.

8. The system of claim 7, wherein the controller is further configured to adjust the acceptable limit for the rate, volume, or patient condition parameter when cerebral herniation is suspected or diagnosed.

9. The system of claim 7, wherein the controller is further configured to adjust the acceptable limit for the rate, volume, or patient condition parameter based on an age of the patient.

10. The system of claim 1, wherein the controller is further configured to cause the visual display to display an acceptable range and measured data for a ventilation rate determined based on the data sensed for the ventilations provided to the patient from the at least one airflow sensor, a ventilation volume determined based on the data sensed for the ventilations provided to the patient from the at least one airflow sensor, and/or for the one or more patient condition parameters.

11. The system of claim 1, wherein the controller is further configured to cause the visual display to display a score for a ventilation rate determined based on the data sensed for the ventilations provided to the patient from the at least one airflow sensor, a ventilation volume determined based on the data sensed for the ventilations provided to the patient from the at least one airflow sensor, and/or for the one or more patient condition parameters.

12. The system of claim 1, wherein the controller is configured to generate, based at least in part on data received from the at least one airflow sensor and/or from the at least one patient condition sensor, a per-parameter metric for ventilation rate or ventilation volume based on the data sensed for the ventilations provided to the patient from the at least one airflow sensor and for each of the one or more patient condition parameters, and to communicate to the user each of the per-parameter metrics along with the first TBI performance metric and the second TBI performance metric.

13. The system of claim 1, wherein the at least one patient condition sensor comprises one or more of a capnometer positioned in the airflow path to sense a concentration of $CO_2$ in the airflow path, a blood oxygen sensor connected to the patient, a blood pressure cuff connected to the patient, or an electrocardiogram sensor.

14. The system of claim 1, wherein the summary information displayed following generation of the second TBI performance metric comprises the first TBI performance metric, the second TBI performance metric, and an overall TBI performance metric based on data for at least the first and second time intervals.

15. The system of claim 1, wherein the controller is configured to update a protocol for calculating a TBI performance metric based on data received from the at least one airflow sensor and/or from the at least one patient condition sensor.

16. The system of claim 15, wherein the second TBI performance metric is generated based on the analysis of the data for the data sensed for the ventilations provided to the patient from the at least one airflow sensor and for the one or more patient condition parameters over the second time interval and on the updated protocol, and wherein the controller is further configured to regenerate the first TBI performance metric based on the updated protocol and the analysis of the received and processed data over a first time interval.

17. The system of claim 1, wherein the controller is configured to determine at least one of a ventilation rate or a ventilation volume for ventilations provided to the patient based on the sensed data for the ventilations provided to the patient from the at least one airflow sensor.

18. The system of claim 17, wherein the controller is further configured to identify when a ventilation is provided to the patient based on the data sensed by the at least one airflow sensor.

19. The system of claim 1, comprising a manual ventilation unit comprising:
the airflow path in fluid communication with the patient's airway,
the at least one airflow sensor positioned in the airflow path, and
a manual ventilation bag configured to provide manual ventilations to the patient through the airflow path.

20. The system of claim 19, wherein the manual ventilation bag comprises a flexible reservoir containing ventilatory gases configured to enable manual ventilation of the patient by a rescuer squeezing the flexible reservoir.

21. The system of claim 1, wherein the controller comprises a processor of a portable defibrillator, the portable defibrillator further comprising a wireless transceiver, and
wherein the visual display comprises a mobile computer device configured to wirelessly receive and display the summary information for the first time interval and the second time interval from the processor of the portable defibrillator by the wireless transceiver.

22. The system of claim 21, wherein the mobile computer device is further configured to receive the data sensed by the at least one airflow sensor and the at least one patient condition sensor by the wireless transceiver of the portable defibrillator, and wherein the mobile computer device is configured to display the first TBI performance metric, the second TBI performance metric, and additional information determined by the mobile computer device based on the received data sensed by the at least one airflow sensor and by the at least one patient condition sensor.

* * * * *